US006849436B2

(12) United States Patent
Bednarik et al.

(10) Patent No.: US 6,849,436 B2
(45) Date of Patent: Feb. 1, 2005

(54) HUMAN HYPOXANTHINE-(GUANINE) PHOSPHORIBOSYL TRANSFERASE-2

(75) Inventors: Daniel P. Bednarik, Columbia, MD (US); Craig A. Rosen, Laytonsville, MD (US); Mark D. Adams, North Potomac, MD (US)

(73) Assignee: Human Genome Sciences, Inc., Rockville, MD (US)

( * ) Notice: Subject to any disclaimer, the term of this patent is extended or adjusted under 35 U.S.C. 154(b) by 324 days.

(21) Appl. No.: 09/902,705

(22) Filed: Jul. 12, 2001

(65) Prior Publication Data

US 2002/0081695 A1 Jun. 27, 2002

Related U.S. Application Data

(63) Continuation of application No. 08/461,031, filed on Jun. 5, 1995, now abandoned, which is a continuation-in-part of application No. PCT/US94/11914, filed on Oct. 19, 1994.

(51) Int. Cl.[7] ........................ C12N 9/10; C12N 5/00; C12P 21/06; C07H 21/04; C07K 17/00

(52) U.S. Cl. .................. 435/193; 435/69.1; 435/320.1; 435/325; 435/252.3; 435/15; 536/23.2; 536/23.1; 530/350

(58) Field of Search ............................... 435/193, 69.1, 435/320.1, 252.3, 15, 325; 530/350; 536/23.2, 23.1

(56) References Cited

U.S. PATENT DOCUMENTS

| | | | |
|---|---|---|---|
| 4,749,570 | A | 6/1988 | Poznanky et al. |
| 5,082,670 | A | 1/1992 | Gage et al. |
| 5,108,921 | A | 4/1992 | Low et al. |
| 5,118,601 | A | 6/1992 | Gruber et al. |
| RE34,387 | E | 9/1993 | Holmes et al. |

FOREIGN PATENT DOCUMENTS

| | | |
|---|---|---|
| WO | WO-94/17183 | 8/1994 |
| WO | WO-97/42320 | 11/1997 |

OTHER PUBLICATIONS

Broun et al. , Science 282:1315–1317, 1998.*

Van de Loo et al. , Proc. Natl. Acad. Sci. 92:6743–6747, 1995.*

Witkowski et al. , Biochemistry 38:11643–11650, 1999.*

Steffernick et al. , J. Bacteriol. 183(8):2405–2410, 2001.*

Harper et al., "Review of Physiological Chemistry, 16th Edition," Lange Medical Publications, Los Altos, pp. 406–408 (1977).

Brown, "Gene Therapy 'Oversold' by Researchers, Journalists," The Washington Post, (Dec. 8, 1995).

U.S. Appl. No. 09/912,292, Rosen et al.

Olson and Milman, "Chinese hamster hypoxanthine–guanine phosphoribosyltransferase," J.Biol Chem., 249(13):4030–4037 (1974).

Biochemistry by A.L. Lehninger, Published by Worth Publishers, Inc., 70 Fifth Ave., NY, NY 10011, pp. 109–122.

1990 Sigma Chemical Company Catalog, (Published by Sigma Chemical Company, P.O. Box 14508, St . Louis, Missouri). P. 1100.

Olaru et al., Revue Roumaine De Biochimie, vol. 18, No. 2, pp. 131–137 (full document) (1981).

Davidson et al., Purine and Pyrimidine Metabolism in Man VII, Part B (Published by Plenum Press, New York, New York) pp. 1–5–108, (1991).

Miller et al., "A transmissible retrovirus expressing human hypoxanthine phosphoribosyltransferase (HPRT): gene transfer into cells obtained from humans deficient in HPRT," Proc. Natl. Acad. Sci. USA, Aug; 80(15):4709–4713, (1983).

Palella et al., "Expression of human HPRT mRNA in brains of mice infected with a recombinant herpes simplex virus–1 vector," Gene, 80(1):137–144, (1989).

Anderson W.F., "Prospects for human gene therapy," Science, 226:401–409 (1984).

Ghangas and Milman, "Radioimmune determination of hypoxanthine phophoribosyltransferase crossreacting material in crythrocytes of Lesch–Nyhan patients," Proc. Natl. Acad. Sci. USA, 72(10):4147–4150, (1975).

Melton et al., "Structure, expression, and mutation of the hypoxanthine phosphoribosyltransferase gene," Proc. Natl. Acad. Sci. USA, 81:2147–2151 (1984).

Jolly et al., "Isolation and charcterization of a full–length expressible cDNA for human hypoxanthine phosphoribosyl transferase," Proc. Natl. Acad. Sci. USA, 80:477–481, (1983).

Patel et al., "Organization of the HPRT gene and related sequences in the human genome," Somatic Cell and Molecular Genetics, 10(5):483–493 (1984).

Scully et al., "A review of the molecular basis of the hypoxanthine–guanine phosphoribosyltransferase (HPRT) deficiency," Hm. Genet., 90:195–207, (1992).

Yip and Balis, "Polyamine–polyphosphate complexes as enzyme inhibitors," Biochemistry, 19:1849–1856 (1980).

(List continued on next page.)

*Primary Examiner*—Rebecca E. Prouty
*Assistant Examiner*—Delia M. Ramirez
(74) *Attorney, Agent, or Firm*—Human Genome Sciences, Inc.

(57) ABSTRACT

A human HPRT-2 polypeptide and DNA (RNA) encoding such polypeptide and a procedure for producing such polypeptide by recombinant techniques is disclosed. Also disclosed are methods for utilizing such polypeptide for the treatment of nephrolithiasis, anemia, precocious gout, kidney stones, Lesch-Nyhan syndrome, renal failure and uricaciduria. Antagonists against such polypeptides and their use as a therapeutic to treat disorders associated with excessive purine synthesis are also disclosed. Diagnostic assays for identifying mutations in nucleic acid sequences encoding a polypeptide of the present invention and for detecting altered levels of the polypeptide of the present invention are also disclosed.

51 Claims, 9 Drawing Sheets

OTHER PUBLICATIONS

Yuan et al., "Steady–state kinetics of the schistosomal hypoxanthine–guanine phosphoribosyltransferase," Biochemistry, 31:806–810, (1992).
Wu and Melton, "Production of a model for Lesch–Nyhan syndrome in hypoxanthine phosphoribosyltransferase–deficient mice," Nature Genetics, 3:235–240, (1993).
Genbank Entry Accession No T00169 (1992).
Genbank Entry Accession No T00115 (1992).
Genbank Entry Accession No T23947 (1994).
Genbank Entry Accession No. T24112 (1994).
Genbank Entry Accession No T24119 (1994).
Genbank Entry Accession No T00696 (1992).
Genbank Entry Accession No T11051 (1993).
Genbank Entry Accession No. T02687 (1993).
Genbank Entry Accession No. T00217 (1992).
Genbank Entry Accession No T00154 (1992).
Genbank Entry Accession No Z47172 (1995).
Genbank Entry Accession No L25928 (1993).
Genbank Entry Accession No L26978 (1995).
Genbank Entry Accession No. A20700 (1994).
Genbank Entry Accession No A20702 (1994).
Genbank Entry Accession No 106859 (1994).
Genbank Entry Accession No L25927 (1993).
Hassett et al., "Characterization of cDNA clones encoding rabbit and human serum paraoxonase: the mature protein retains its signal sequence," Biochemistry, 30(42):10141–10149, (1991).
Adkins et al., "Molecular basis for the polymorphic forms of human serum paraoxonase/arytesterase: glutamine or arginine at position 191, for the respective A or B allozymes," Am. J. Hum. Genet., 52:598–608, (1993).
Johnson et al., Biological Abstracts, 69(7):4678, (1980).

* cited by examiner

```
  1 GAT TTT TTG TGA TAT CTT CTT CGG GGG GGG GGG GAA CCT ATT GTA TAA ACG CCA ACC AAC CGG

 64 CCC TTT TTT GGG TAC CTG GCC ATT TTA CTT GGC CCA TTT TGG TAA AAT GTT CCT TTC CCT GCG

127 TTA ATC CCC CTG ATT CCT TGT GGG ATA ACC CGT ATT CCC CCC CTT AGA GTG AAT TTG AAA ACC

190 CTT TCG CCC GGA AGG GGA CCG ACC GAG CCC AGC GAT TCA TGG AGC GAG GAA AGC GGG AAG AGC

253 GCC CAA TAC CCA AGC CGC CTC TCG CCG GCG CGT TGT GCG ATT CAT TAA TAC AGC TGC CAC GAC

316 AGG TTT CCC GAC TGG AAA GCG GTC AGT GAG CGC AAC ACA ATT AAT GTG AGT TAG CTC ACT CAT

379 TAG GCA CCC CAG GCT TTA CAC TTT ATG CTT CCG GCT CGT ATG TTG TGT GGA ATT GTG AGC GGA

442 TAA CAA TTT CAC ACA GGA AAC AGC TAT GAC CAT GAT TAC GTC CAA GCT CGA AAT TAA CCC TCA

505 CTA AAG GGA ACA AAA ACT GGA GCT CCA CCG CGG TGG CGG CCG CTC TAG AAC TAG TGG ATC CCC

568 CGG GCT CCA GGA ATT CGC CAC GAC CGG GAG GAC CGA GGA GGC GCC AGA CTA CGG GCG A   ATG
                                                                                    MET

629 GCG ACC CGC AGC CCT GGC GTC GTG ATT ATG GAT GAT TGG CCA GGG TAT GAC TTG AAT TTA TTC
    Ala Thr Arg Ser Pro Gly Val Val Ile MET Asp Asp Trp Pro Gly Tyr Asp Leu Asn Leu Phe
```

FIG. 1A

```
692  ACG TAC CCA CAG CAC TAT TAT GGA GAC TTG GAG TAT GTC CTC ATC CCT CAT GGT ATC ATT GTG
     Thr Tyr Pro Gln His Tyr Tyr Gly Asp Leu Glu Tyr Val Leu Ile Pro His Gly Ile Ile Val

755  GAC AGA ATT GAG CGG CTG GCC AAG GAT ATT ATG AAA GAC ATA GGA TAT AGT GAC ATC ATG GTC
     Asp Arg Ile Glu Arg Leu Ala Lys Asp Ile MET Lys Asp Ile Gly Tyr Ser Asp Ile MET Val

818  CTG TGT GTG CTT AAA GGG GGG TAC AAA TTC TGT GCT GAT CTC GTA GAA CAC CTT AAG AAC ATC
     Leu Cys Val Leu Lys Gly Gly Tyr Lys Phe Cys Ala Asp Leu Val Glu His Leu Lys Asn Ile

881  AGC CGA AAT TCA GAT CGG TTT GTC TCA ATG AAG GTT GAT TTC ATC AGA CTA AAA AGT TAC AGG
     Ser Arg Asn Ser Asp Arg Phe Val Ser MET Lys Val Asp Phe Ile Arg Leu Lys Ser Tyr Arg

944  AAT GAC CAG TCC ATG GGT GAG ATG CAG ATA ATC GGA GGC GGT GAT CTT TCA ACG CTG GCT GGA
     Asn Asp Gln Ser MET Gly Glu MET Gln Ile Ile Gly Gly Gly Asp Leu Ser Thr Leu Ala Gly

1007 AAG AAT TTT CTC ATT GTT GAG GAT GTT GTC GGA ACT GGG AGG ACC ATG AAA GCA CTA CTC AGC
     Lys Asn Phe Leu Ile Val Glu Asp Val Val Gly Thr Gly Arg Thr MET Lys Ala Leu Leu Ser

1070 AAT ATA GAG AAA TAC AAG CCC AAC ATG ATT AAG GTA GCC AGT TTG TTG GTG AAG AGA ACA TCC
     Asn Ile Glu Lys Tyr Lys Pro Asn MET Ile Lys Val Ala Ser Leu Leu Val Lys Arg Thr Ser

1133 AGA AGT GAC GGC TTT AGA CCT GAC TAT GCT GGA TTT GAG ATT CCA CAC TTA TTT GTG GTG GGA
     Arg Ser Asp Gly Phe Arg Pro Asp Tyr Ala Gly Phe Glu Ile Pro His Leu Phe Val Val Gly
```

FIG. 1B

```
1196 TAT GCC TTA GAT TAC AAT GAA TAC TTC AGA GAT CTG AAT CAC ATA TGC GTC ATC AAT GAG CAC
     Tyr Ala Leu Asp Tyr Asn Glu Tyr Phe Arg Asp Leu Asn His Ile Cys Val Ile Asn Glu His

1259 GGG TAA AGG AAA ATA TCG AGT CTT AAA GAC ATG AAT TCT CAC CAC TAA AGG CCC CAG ATA GGA
     Gly STP

1322 TCA TTT TTA CGC CTG TCT TGG GGA GCC AGT TGC AAG TTG GGC CCC CCC GGA TCT TCA TCA GGA

```
1    MATRSPGVVISDDEPGYDLDLFCIPNHYAEDLERVFIPHGLIMDRTERLARDVMKE   56
1    MATRSPGVVIMDDWPGYDLNLFTYPQHYYGDLEYVLIPHGIIVDRIERLAKDIMKD   56

57   MGGHHIVALCVLKGGYKFFADLLDYIKALNRNSDRSIPMTVDFIRLKSYCNDQSTG   112
57   IGYSDIMVLCVLKGGYKFCADLVEHLKNISRNSDRFVSMKVDFIRLKSYRNDQSMG   112

113  DIKVIGGDDLSTLTGKNVLIVEDIIDTGKTMQTLLSLVRQYNPKMVKVASLLVKRT   168
113  EMQIIGGGDLSTLAGKNFLIVEDVVGTGRTMKALLSNIEKYKPNMIKVASLLVKRT   168

169  PRSVGYKPDFVGFEIPDKFVVGYALDYNEYFRDLNHVCVISETGKAKYKA         218
169  SRSDGFRPDYAGFEIPHLFVVGYALDYNEYFRDLNHICVINEHG               212
```

FIG. 2

```
     MATRS-PGV--------VISDDEPGYDLDLF  Majority
              10        20        30
 1   MATRS-PGV--------VIMDDWPGYDLNLF  HPRT2b.pep
 1   MATRS-PGV--------VISDDEPGYDLDLF  HPRThu
 1   MATRS-PSV--------VISDDEPGYDLDLF  HPRTcl
 1   MPIPNNPGAGENAFDPVFVKDDDGYDLDSF  HPRTplas
 1   MEPACK-------------------YD--F  HPRTtrypan

     CIPNHYXEDLEKVLIPHGVIMDRIERLARD  Majority
              40        50        60
23   TYPQHYYGDLEYVLIPHGIIVDRIERLAKD  HPRT2b.pep
23   CIPNHYAEDLERVFIPHGLIMDRTERLARD  HPRThu
23   CIPNHYVEDLEKVFIPHGVIMDRTERLARD  HPRTcl
31   MIPAHYKKYLTKVLVPNGVIKNRIEKLAYD  HPRTplas
10   ATSVLFTEAELHTRM-RGVAQRIADDYSNC  HPRTtrypan

     VMKEMGGHHIVALCVLKGGYKFFADLLDHL  Majority
              70        80        90
53   IMKDIGYSDIMVLCVLKGGYKFCADLVEHL  HPRT2b.pep
53   VMKEMGGHHIVALCVLKGGYKFFADLLDYI  HPRThu
53   VMKEMGGHHIVALCVLKGGYKFFADLLDYI  HPRTcl
61   IKKVYNNEEFHILCLLKGSRGFFTALLKHL  HPRTplas
39   NLKPLE-NPLVIVSVLKGSFVFTADMVRIL  HPRTtyrpan
```

FIG.3A

```
                          100                 110                 120
    K A L N R N S D R S V P M T V - - - D F I R L K S Y C N D Q  Majority
83  K N I S R N S D R F V S M K V - - - D F I R L K S Y R N D Q  HPRT2b.pep
83  K A L N R N S D R S I P M T V - - - D F I R L K S Y C N D Q  HPRThu
83  K A L N R N S D R S I P M T V - - - D F I R L K S Y C N D Q  HPRTcl
91  S R I H N Y S A V E M S K P L F G E H Y V R V K S Y C N D Q  HPRTplas
68  G D F G - - - - - - V P T R V - - - E F L R A S S Y G H D T  HPRTtrypan
```

```
                          130                 140                 150
    S T G D I K V I G G D D L S T L T G K N V L I V E D I I D T  Majority
110 S M G E M Q I I G G G D L S T L A G K N F L I V E D V V G T  HPRT2b.pep
110 S T G D I K V I G G D D L S T L T G K N V L I V E D I I D T  HPRThu
110 S T G D I K V I G G D D L S T L T G K N V L I V E D I I D T  HPRTcl
121 S T G T L E I V S - E D L S C L K G K H V L I V E D I I D T  HPRTplas
89  K S C G R V D V K A D G L C D I R G K H V L V L E D I L D T  HPRTtrypan
```

```
                          160                 170                 180
    G K T M Q T L L S L V K K Y E P K M V K V A S L L V K R T S  Majority
140 G R T M K A L L S N I E K Y K P N M I K V A S L L V K R T S  HPRT2b.pep
140 G K T M Q T L L S L V R Q Y N P K M V K V A S L L V K R T P  HPRThu
140 G K T M Q T L L S L V K R Y N P K M V K V A S L L V K R T S  HPRTcl
150 G K T L V K F C E Y L K K F E I K T V A I A C L F I K R T P  HPRTplas
119 A L T L R E V V D S L K K S E P A S I K T L V A I D K P G G  HPRTtrypan
```

FIG.3B

```
    R S V G F K P D F V G F E I P D K F V V G Y A L D Y N E Y F  Majority
                      190                 200                 210
170 R S D G F R P D Y A G F E I P H L F V V G Y A L D Y N E Y F  HPRT2b.pep
170 R S V G Y K P D F V G F E I P D K F V V G Y A L D Y N E Y F  HPRThu
170 R S V G Y R P D F V G F E I P D K F V V G Y A L D Y N E Y F  HPRTcl
180 L W N G F K A D F V G F S I P D H F V V G Y S L D Y N E I F  HPRTplas
149 R K I P F T A E Y V V A D V P N V F V V G Y G L D Y D Q S Y  HPRTtrypan

    R D L N H V C V I S - - - - - - - - - - E T G K A K Y K A - -  Majority
                      220                 230                 240
200 R D L N H I C V I N - - - - - - - - - - E H G                  HPRT2.pep
200 R D L N H V C V I S - - - - - - - - - - E T G K A K Y K A      HPRThu
200 R D L N H I C V I S - - - - - - - - - - E T G K A K Y K A      HPRTcl
210 R D L D H C C L V N - - - - - - - - - - D E G K K K Y K A T S  HPRTplas
179 R E V R D V V I L K P S V Y E T W G K E L E R R K A A G E A    HPRTtrypan

    - -                                                            Majority

212                                                                HPRT2b.pep
218                                                                HPRThu
218                                                                HPRTcl
231 L                                                              HPRTplas
209 K R                                                            HPRTtrypan
```

FIG.3C

HUMAN HYPOXANTHINE-(GUANINE) PHOSPHORIBOSYL TRANSFERASE-2

CROSS REFERENCE TO RELATED APPLICATIONS

This application is a continuation of and claims priority under 35 U.S.C. § 120 to U.S. application Ser. No. 08/461,031, filed Jun. 5, 1995, now abandoned, which is a continuation-in-part of and claims priority under 35 U.S.C. § 120 to International Application No. PCT/US94/11914, filed on Oct. 19, 1994, (which International Application was published by the International Bureau in the English language on May 2, 1996 as International Publication No. WO 96/12501), both of which are hereby incorporated by reference in their entirety.

FIELD OF THE INVENTION

This invention relates to newly identified polynucleotides, polypeptides encoded by such polynucleotides, the use of such polynucleotides and polypeptides, as well as the production of such polynucleotides and polypeptides. More particularly, the polypeptide of the present invention is human hypoxanthine-(guanine) phosphoribosyl transferase-2, sometimes hereinafter referred to as "HPRT-2". The invention also relates to inhibiting the action of such polypeptides.

BACKGROUND OF THE INVENTION

In higher animals, nucleases are secreted by the pancreas and enzymatically hydrolyze nucleic acids to yield, ultimately, the free purine and pyrimidine bases. If not salvaged and re-used, the free bases are degraded further and the end-products excreted. In some vertebrates, including the primates, the dalmatian dog, birds and some reptiles, the end-product of purine degradation is uric acid, whereas in other mammals and reptiles, and also in mollusks, the end-product is allantoin.

The degradation of purines to the end-product, uric acid in man has been intensively studied, since genetic aberrations of this pathway are known. The major purines, adenine and guanine, are first converted into xanthine, which is then oxidized by the complex flavoprotein xanthine oxidase to uric acid and a superoxide radical which undergoes conversion to hydrogen peroxide by the action of superoxide dismutase. In the presence of HPRT, however, a phosphoribosyl group is added to adenine and guanine from PRPP (phosphoribosyl pyrophosphate) to form AMP or GMP with the simultaneous loss of pyrophosphate ($PP_i$), and these may be re-used.

Isotopic studies on vertebrates that excrete uric acid have shown it to derive from both exogenous and endogenous nucleic acids. Only about 0.5 grams of uric acid is excreted daily by the normal person, although up to 5 grams of free purines are formed daily. Evidently, the greater part of the free purines are salvaged or recycled. Uric acid is present in blood largely as monosodium urate, however, both the free acid and the urate salts are relatively insoluble in water, with the result that in some individuals uric acid precipitates and crystallizes in the urine, subsequently forming kidney stones and causing damage to this organ. Uric acid deposits are also formed in cartilaginous tissues, to produce gout, which apparently results from over-production of uric acid. This disease can be alleviated by treatment with the drug allopurinol. Allopurinol is an analog of hypoxanthine. Allopurinol inhibits xanthine oxidase and thus decreases the formation and accumulation of uric acid.

The salvage of purines in mammalian cells is facilitated by the conversion of hypoxanthine (adenine) and guanine to their respective mononucleotide forms, IMP and GMP by HPRT via an ordered, bi-bi reaction mechanism (Davidson, B. L., et al., J. Biol. Chem., 264:520–525 (1989)). A total defect in this gene is the cause of Lesch-Nyhan Syndrome in humans, which is marked by severe retardation, hyperuricemia, hyperuricaciduria, and severe neurological dysfunction (Kelley, W. N., et al., Science, 155:1682–1684 (1967)). Partial loss of this activity results in the overproduction of uric acid which subsequently leads to precocious gout and uric acid nephrolithiasis.

BRIEF SUMMARY OF THE INVENTION

Applicants have discovered an HPRT-2 gene which has been transfected into a heterologous expression system, producing a protein with properties consistent with its characterization as a member of the HPRT family.

Sequencing inaccuracies are a common problem when attempting to determine polynucleotide sequences. Accordingly, the sequence of FIGS. 1A–C is based on several sequencing runs and the sequencing accuracy is considered to be at least 97%.

In accordance with one aspect of the present invention, there is provided a novel putative mature polypeptide which is HPRT-2, as well as fragments, analogs and derivatives thereof. The polypeptide of the present invention is of human origin.

In accordance with another aspect of the present invention, there are provided polynucleotides (DNA or RNA) which encode such polypeptides.

In accordance with yet a further aspect of the present invention, there is provided a process for producing such polypeptides by recombinant techniques.

In accordance with yet a further aspect of the present invention, there is provided a process for utilizing such polypeptides, or polynucleotides encoding such polypeptides for therapeutic purposes, for example, to treat Lesch-Nyhan syndrome, precocious gout, uric acid nephrolithiasis, uricaciduria, renal failure (nephropathy), kidney stones and anemia.

In accordance with yet a further aspect of the present invention, there are provided antibodies against such polypeptides.

In accordance with yet another aspect of the present invention, there are provided antagonists to such polypeptides, which may be used to inhibit the action of such polypeptides, for example, in the treatment of African Sleeping sickness, obesity, advanced primary renal diseases, myocardial infarction, hypertension, hypo- and hyperparathyroidism, psoriasis, myxedema and proliferative hematopoietic disease.

These and other aspects of the present invention should be apparent to those skilled in the art from the teachings herein.

BRIEF DESCRIPTION OF THE DRAWINGS

The following drawings are illustrative of embodiments of the invention and are not meant to limit the scope of the invention as encompassed by the claims.

FIGS. 1A–C show the cDNA sequence (SEQ ID NO:1) and corresponding deduced amino acid sequence (SEQ ID NO:2) of HPRT-2. The region of the nucleotide sequence underlined represents the translated region and the mature region of the amino acid sequence translated from the nucleotide sequence. Sequencing of the 1,368 bp EcoRI- XhoI cDNA insert from pBlueScript was performed in both directions. The start site is denoted by the methionine located at nucleotide position 626.

FIG. 2 shows an alignment of amino acid sequences between Human HPRT (top line; SEQ ID NO:7) and HPRT-2 (bottom line; SEQ ID NO:2). An in-frame termination codon for HPRT-2 is denoted by an asterisk at amino acid 213. The protein alignment was performed using GCG bestfit analysis.

FIGS. 3A–C show an alignment of the amino acid sequences of other HPRT enzymes with HPRT-2 (SEQ ID NO:2). The clustal program (Higgins, D. G. and Sharp. P. M., Gene, 73:237–244 (1988)) was employed to align the HPRT peptide sequences from human (HPRThu; SEQ ID NO:7), *C. longicaudatus* (HPRTcl; SEQ ID NO:8), *Plasmodium falciparum* (HPRTplas; SEQ ID NO:9), and *Trypanosoma brucei* (HPRTtrypan; SEQ ID NO:10) with HPRT-2 (HPRT-2b.pep; SEQ ID NO:2). Identical amino acids are identified by black shading.

DETAILED DESCRIPTION

Figure 4:
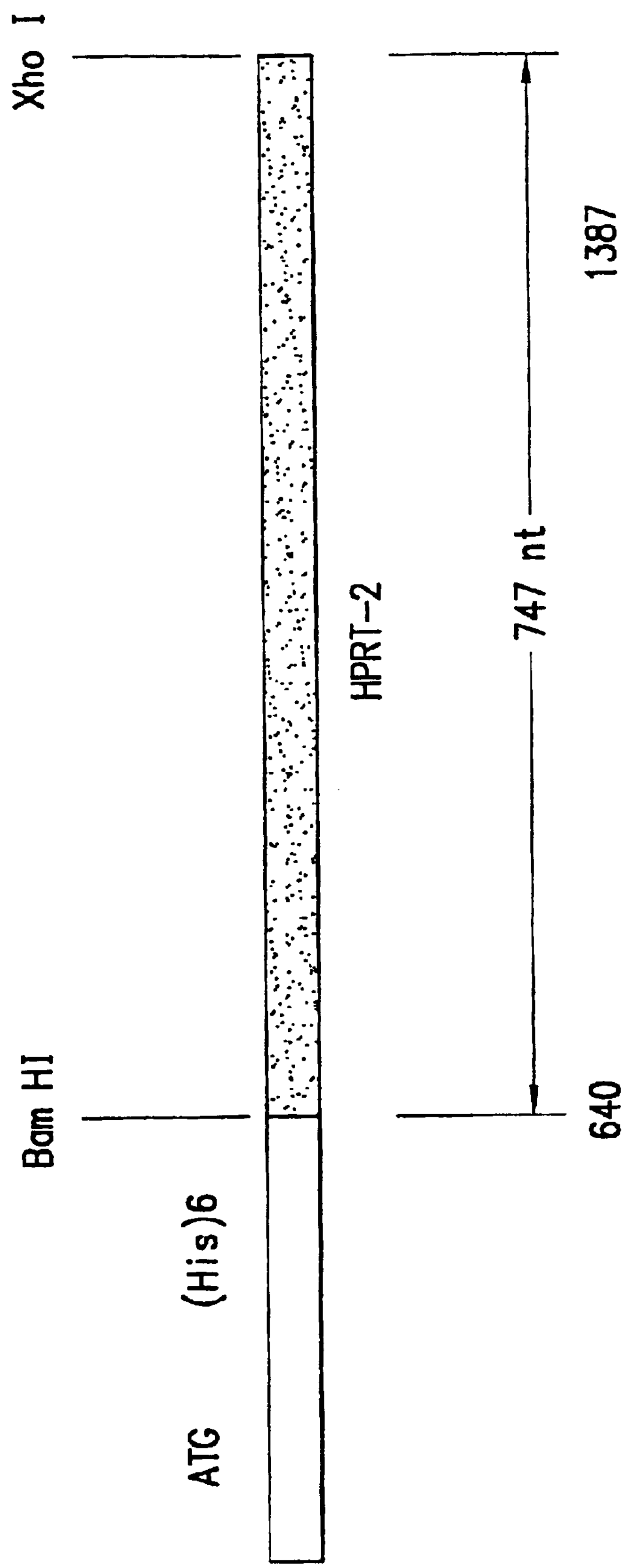
FIG. 4 is a schematic representation of the pTrcHIS plasmid after ligation of the HPRT-2 gene.
Figure 5:
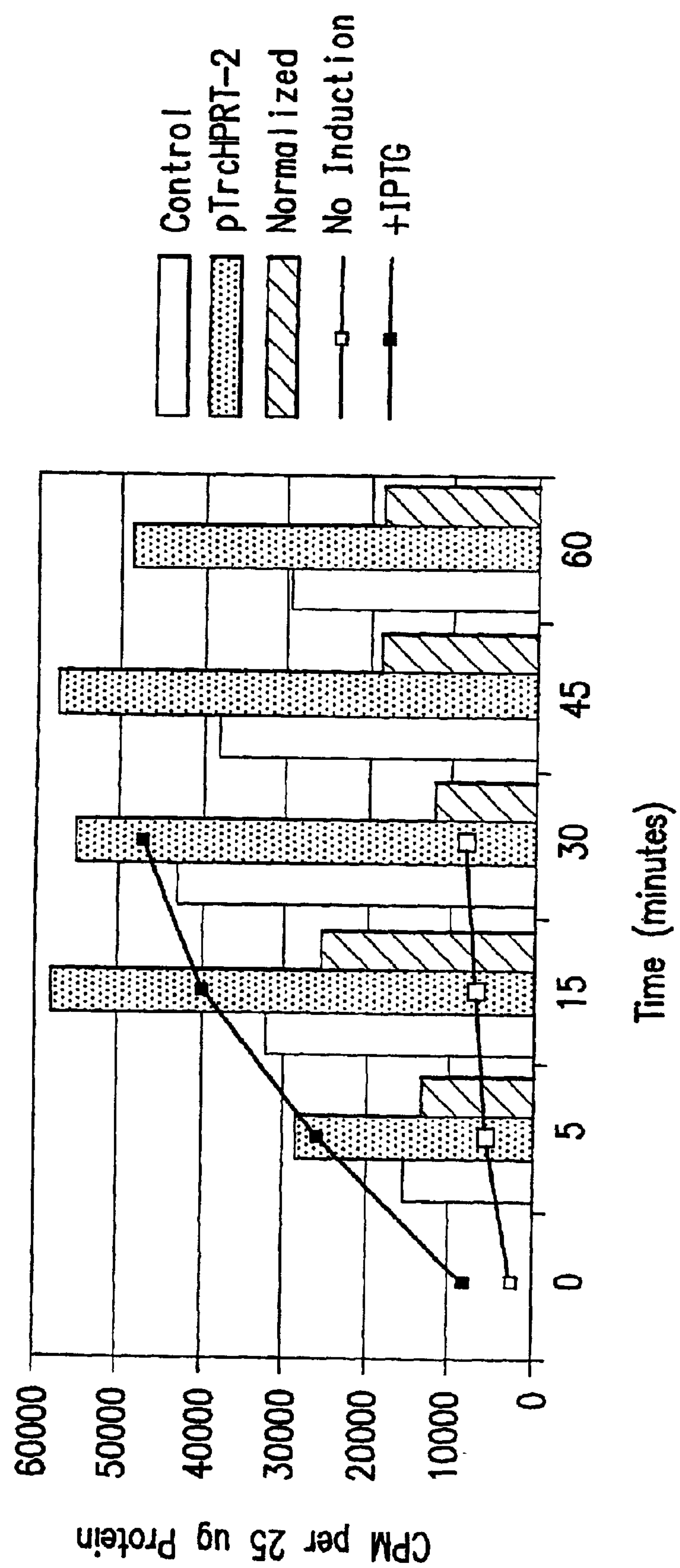
FIG. 5 is a graph depicting the results of an enzymatic activity assay of HPRT-2. The bar graph (diagonal lines) shows the induced HPRT-2 activity, which was normalized to subtract background HPRT activity. Sϕ606 *E. Coli* cells, which contain no inherent HPRT activity, were transformed with pTrcHISHPRT-2 and induced with IPTG (linegraph, closed squares). Uninduced Sϕ606 cells (linegraph, open squares) showed low levels of HPRT-2 activity.

In accordance with one aspect of the present invention there is provided an isolated nucleic acid (polynucleotide) which encodes for the mature polypeptide having the deduced amino acid sequence of FIGS. 1A–C (SEQ ID NO:2) or for the mature polypeptide encoded by the cDNA of the clone deposited with the American Type Culture Collection ("ATCC"), 10801 University Boulevard, Manassas, Va. 20110-2209, USA, as ATCC Deposit No. 75844 on Jul. 27, 1994. The clone is being maintained under the terms of the Budapest Treaty and will be made available to a patent office signatory to the Budapest Treaty.

A polynucleotide encoding a polypeptide of the present invention was discovered in a cDNA library derived from a human fetal lung. It is structurally related to the HPRT family. It contains an open reading frame encoding a protein of 212 amino acid residues (SEQ ID NO:2). The protein exhibits the highest degree of homology to Human HPRT (SEQ ID NO:7) with 66% identity and 79.7% similarity. The PRPP-binding motif positions 141 to 153 (FLIVEDVVGTGR) of FIG. 2 maintains similarity with regard to adjacent glutamate and aspartate residues both of which have carboxyl moieties which have been shown to bind to the 5' phosphate group of PRPP. The lysine at position 153 is replaced by arginine, a similar basic amino acid which is thought to be involved in catalysis. The binding of guanine or hypoxanthine exocyclic 06 by lysine-165 and the exocyclic N2 by valine-187 and aspartate-193 was shown to be essential for purine substrate specificity as reflected by conservation across species. Sequence analysis of HPRT-2 demonstrates conservation of these essential amino acid moieties at positions lysine-177, valine-199 and aspartate-205.

The polynucleotide of the present invention may be in the form of RNA or in the form of DNA, which DNA includes cDNA, genomic DNA, and synthetic DNA. The DNA may be double-stranded or single-stranded, and if single stranded may be the coding strand or non-coding (anti-sense) strand. The coding sequence which encodes the mature polypeptide may be identical to the coding sequence shown in FIGS. 1A–C (SEQ ID NO:1) or that of the deposited clone or may be a different coding sequence which coding sequence, as a result of the redundancy or degeneracy of the genetic code, encodes the same mature polypeptide as the DNA of FIGS. 1A–C (SEQ ID NO:1) or the deposited cDNA.

The polynucleotide which encodes for the mature polypeptide of FIGS. 1A–C (SEQ ID NO:2) or for the mature polypeptide encoded by the deposited cDNA may include: only the coding sequence for the mature polypeptide; the coding sequence for the mature polypeptide (and optionally additional coding sequence) and non-coding sequence, such as introns or non-coding sequence 5' and/or 3' of the coding sequence for the mature polypeptide.

Thus, the term "polynucleotide encoding a polypeptide" encompasses a polynucleotide which includes only coding sequence for the polypeptide as well as a polynucleotide which includes additional coding and/or non-coding sequence.

The present invention further relates to variants of the hereinabove described polynucleotides which encode for fragments, analogs and derivatives of the polypeptide having the deduced amino acid sequence of FIGS. 1A–C (SEQ ID NO:2) or the polypeptide encoded by the cDNA of the deposited clone. The variant of the polynucleotide may be a naturally occurring allelic variant of the polynucleotide or a non-naturally occurring variant of the polynucleotide.

Thus, the present invention includes polynucleotides encoding the same mature polypeptide as shown in FIGS. 1A–C (SEQ ID NO:2) or the same mature polypeptide encoded by the cDNA of the deposited clone as well as variants of such polynucleotides which variants encode for a fragment, derivative or analog of the polypeptide of FIGS. 1A–C (SEQ ID NO:2) or the polypeptide encoded by the cDNA of the deposited clone. Such nucleotide variants include deletion variants, substitution variants and addition or insertion variants.

As hereinabove indicated, the polynucleotide may have a coding sequence which is a naturally occurring allelic variant of the coding sequence shown in FIGS. 1A–C (SEQ ID NO:1) or of the coding sequence of the deposited clone. As known in the art, an allelic variant is an alternate form of a polynucleotide sequence which may have a substitution, deletion or addition of one or more nucleotides, which does not substantially alter the function of the encoded polypeptide.

The polynucleotides of the present invention may have the coding sequence fused in frame to a marker sequence which allows for purification of the polypeptide of the present invention. The marker sequence may be a hexahistidine tag supplied by a pTrcHIS(A) vector to provide for purification of the mature polypeptide fused to the marker in the case of a bacterial host, or, for example, the marker sequence may be a hemagglutinin (HA) tag when a mammalian host, e.g. COS-7 cells, is used. The HA tag corresponds to an epitope derived from the influenza hemagglutinin protein (Wilson, I., et al., Cell, 37:767 (1984)).

The term "gene" means the segment of DNA involved in producing a polypeptide chain; it includes regions preceding and following the coding region (leader and trailer) as well as intervening sequences (introns) between individual coding segments (exons).

Fragments of the full length gene of the present invention may be used as a hybridization probe for a cDNA library to isolate the full length cDNA and to isolate other cDNAs which have a high sequence similarity to the gene or similar biological activity. Probes of this type preferably have at least 30 bases and may contain, for example, 50 or more bases. The probe may also be used to identify a cDNA clone corresponding to a full length transcript and a genomic clone or clones that contain the complete gene including regulatory and promoter regions, exons, and introns. An example of a screen comprises isolating the coding region of the gene by using the known DNA sequence to synthesize an oligonucleotide probe. Labeled oligonucleotides having a sequence complementary to that of the gene of the present invention are used to screen a library of human cDNA, genomic DNA or mRNA to determine which members of the library the probe hybridizes to.

The present invention further relates to polynucleotides which hybridize to the hereinabove-described sequences if there is at least 70%, preferably at least 90%, and more preferably at least 95% identity between the sequences. The present invention particularly relates to polynucleotides which hybridize under stringent conditions to the hereinabove-described polynucleotides. As herein used, the term "stringent conditions" means hybridization will occur only if there is at least 95% and preferably at least 97% identity between the sequences. The polynucleotides which hybridize to the hereinabove described polynucleotides in a preferred embodiment encode polypeptides which either retain substantially the same biological function or activity as the mature polypeptide encoded by the cDNAs of FIGS. 1A–C (SEQ ID NO: 1) or the deposited cDNA.

Alternatively, the polynucleotide may have at least 20 bases, preferably 30 bases, and more preferably at least 50 bases which hybridize to a polynucleotide of the present invention and which has an identity thereto, as hereinabove described, and which may or may not retain activity. For example, such polynucleotides may be employed as probes for the polynucleotide of SEQ ID NO:1, for example, for recovery of the polynucleotide or as a diagnostic probe or as a PCR primer.

Thus, the present invention is directed to polynucleotides having at least a 90% and more preferably at least a 95% identity to a polynucleotide which encodes the polypeptide of SEQ ID NO:2 as well as fragments thereof, which fragments have at least 30 bases and preferably at least 50 bases and to polypeptides encoded by such polynucleotides.

The deposit(s) referred to herein will be maintained under the terms of the Budapest Treaty on the International Recognition of the Deposit of Micro-organisms for purposes of Patent Procedure. These deposits are provided merely as convenience to those of skill in the art and are not an admission that a deposit is required under 35 U.S.C. §112. The sequence of the polynucleotides contained in the deposited materials, as well as the amino acid sequence of the polypeptides encoded thereby, are incorporated herein by reference and are controlling in the event of any conflict with any description of sequences herein. A license may be required to make, use or sell the deposited materials, and no such license is hereby granted.

The present invention further relates to a HPRT-2 polypeptide which has the deduced amino acid sequence of FIGS. 1A–C (SEQ ID NO:2) or which has the amino acid sequence encoded by the deposited cDNA, as well as fragments, analogs and derivatives of such polypeptide.

The terms "fragment," "derivative" and "analog" when referring to the polypeptide of FIGS. 1A–C (SEQ ID NO:2) or that encoded by the deposited cDNA, means a polypeptide which retains essentially the same biological function or activity as such polypeptide. Thus, an analog includes a proprotein which can be activated by cleavage of the proprotein portion to produce an active mature polypeptide.

The polypeptide of the present invention may be a recombinant polypeptide, a natural polypeptide or a synthetic polypeptide, preferably a recombinant polypeptide.

The fragment, derivative or analog of the polypeptide of FIGS. 1A–C (SEQ ID NO:2) or that encoded by the deposited cDNA may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which the mature polypeptide is fused with another compound, such as a compound to increase the half-life of the polypeptide (for example, polyethylene glycol), or (iv) one in which the additional amino acids are fused to the mature polypeptide which is employed for purification of the mature polypeptide or a proprotein sequence. Such fragments, derivatives and analogs are deemed to be within the scope of those skilled in the art from the teachings herein.

The polypeptides and polynucleotides of the present invention are preferably provided in an isolated form, and preferably are purified to homogeneity.

The term "isolated" means that the material is removed from its original environment (e.g., the natural environment if it is naturally occurring). For example, a naturally-occurring polynucleotide or polypeptide present in a living animal is not isolated, but the same polynucleotide or polypeptide, separated from some or all of the coexisting materials in the natural system, is isolated. Such polynucleotides could be part of a vector and/or such polynucleotides or polypeptides could be part of a composition, and still be isolated in that such vector or composition is not part of its natural environment.

The polypeptides of the present invention include the polypeptide of SEQ ID NO:2 (in particular the mature polypeptide) as well as polypeptides which have at least 80% similarity (preferably at least 70% identity) to the polypeptide of SEQ ID NO:2 and more preferably at least 90% similarity (more preferably at least 90% identity) to the polypeptide of SEQ ID NO:2 and still more preferably at least 95% similarity (still more preferably at least 95% identity) to the polypeptide of SEQ ID NO:2 and also include portions of such polypeptides with such portion of the polypeptide generally containing at least 30 amino acids and more preferably at least 50 amino acids.

As known in the art "similarity" between two polypeptides is determined by comparing the amino acid sequence and its conserved amino acid substitutes of one polypeptide to the sequence of a second polypeptide.

Fragments or portions of the polypeptides of the present invention may be employed for producing the corresponding full-length polypeptide by peptide synthesis; therefore, the fragments may be employed as intermediates for producing the full-length polypeptides. Fragments or portions of the polynucleotides of the present invention may be used to synthesize full-length polynucleotides of the present invention.

The present invention also relates to vectors which include polynucleotides of the present invention, host cells which are genetically engineered with vectors of the invention and the production of polypeptides of the invention by recombinant techniques.

Host cells are genetically engineered (transduced or transformed or transfected) with the vectors of this invention which may be, for example, a cloning vector or an expression vector. The vector may be, for example, in the form of a plasmid, a viral particle, a phage, etc. The engineered host cells can be cultured in conventional nutrient media modified as appropriate for activating promoters, selecting transformants or amplifying the HPRT-2 genes. The culture conditions, such as temperature, pH and the like, are those previously used with the host cell selected for expression, and will be apparent to the ordinarily skilled artisan.

The polynucleotides of the present invention may be employed for producing polypeptides by recombinant techniques. Thus, for example, the polynucleotide may be included in any one of a variety of expression vectors for expressing a polypeptide. Such vectors include chromosomal, nonchromosomal and synthetic DNA sequences, e.g., derivatives of SV40; bacterial plasmids; phage DNA; baculovirus; yeast plasmids; vectors derived from combinations of plasmids and phage DNA, viral DNA such as vaccinia, adenovirus, fowl pox virus, and pseudorabies. However, any other vector may be used as long as it is replicable and viable in the host.

The appropriate DNA sequence may be inserted into the vector by a variety of procedures. In general, the DNA sequence is inserted into an appropriate restriction endonuclease site(s) by procedures known in the art. Such procedures and others are deemed to be within the scope of those skilled in the art.

The DNA sequence in the expression vector is operatively linked to an appropriate expression control sequence(s) (promoter) to direct mRNA synthesis. As representative examples of such promoters, there may be mentioned: LTR or SV40 promoter, the *E. coli.* lac or trp, the phage lambda $P_L$ promoter and other promoters known to control expression of genes in prokaryotic or eukaryotic cells or their viruses. The expression vector also contains a ribosome binding site for translation initiation and a transcription terminator. The vector may also include appropriate sequences for amplifying expression.

In addition, the expression vectors preferably contain one or more selectable marker genes to provide a phenotypic trait for selection of transformed host cells such as dihydrofolate reductase or neomycin resistance for eukaryotic cell culture, or such as tetracycline or ampicillin resistance in *E. coli.*

The vector containing the appropriate DNA sequence as hereinabove described, as well as an appropriate promoter or control sequence, may be employed to transform an appropriate host to permit the host to express the protein.

As representative examples of appropriate hosts, there may be mentioned: bacterial cells, such as *E. coli, Streptomyces, Salmonella typhimurium;* fungal cells, such as yeast; insect cells such as *Drosophila* and *Spodoptera* Sf9; animal cells such as CHO, COS or Bowes melanoma; adenoviruses; plant cells, etc. The selection of an appropriate host is deemed to be within the scope of those skilled in the art from the teachings herein.

More particularly, the present invention also includes recombinant constructs comprising one or more of the sequences as broadly described above. The constructs comprise a vector, such as a plasmid or viral vector, into which a sequence of the invention has been inserted, in a forward or reverse orientation. In a preferred aspect of this embodiment, the construct further comprises regulatory sequences, including, for example, a promoter, operably linked to the sequence. Large numbers of suitable vectors and promoters are known to those of skill in the art, and are commercially available. The following vectors are provided by way of example. Bacterial: pQE70, pQE60, pQE-9 (Qiagen), pBS, pD10, phagescript, psiX174, pBluescript SK, pBSKS, pNH8A, pNH16a, pNH18A, pNH46A (Stratagene); ptrc99a, pKK223-3, pKK233-3, pDR540, pRIT5 (Pharmacia). Eukaryotic: pWLNEO, pSV2CAT, pOG44, pXT1, pSG (Stratagene) pSVK3, pBPV, pMSG, pSVL (Pharmacia). However, any other plasmid or vector may be used as long as they are replicable and viable in the host.

Promoter regions can be selected from any desired gene using CAT (chloramphenicol transferase) vectors or other vectors with selectable markers. Two appropriate vectors are PKK232-8 and PCM7. Particular named bacterial promoters include lacI, lacZ, T3, T7, gpt, lambda $P_R$, $P_L$ and trp. Eukaryotic promoters include CMV immediate early, HSV thymidine kinase, early and late SV40, LTRs from retrovirus, and mouse metallothionein-I. Selection of the appropriate vector and promoter is well within the level of ordinary skill in the art.

In a further embodiment, the present invention relates to host cells containing the above-described constructs. The host cell can be a higher eukaryotic cell, such as a mammalian cell, or a lower eukaryotic cell, such as a yeast cell, or the host cell can be a prokaryotic cell, such as a bacterial cell. Introduction of the construct into the host cell can be effected by calcium phosphate transfection, DEAE-Dextran mediated transfection, or electroporation (Davis, L., Dibner, M., Battey, I., Basic Methods in Molecular Biology, (1986)).

The constructs in host cells can be used in a conventional manner to produce the gene product encoded by the recombinant sequence. Alternatively, the polypeptides of the invention can be synthetically produced by conventional peptide synthesizers.

Mature proteins can be expressed in mammalian cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook, et al., Molecular Cloning: A Laboratory Manual, Second Edition, Cold Spring Harbor, N.Y., (1989), the disclosure of which is hereby incorporated by reference.

Transcription of the DNA encoding the polypeptides of the present invention by higher eukaryotes is increased by inserting an enhancer sequence into the vector. Enhancers are cis-acting elements of DNA, usually about from 10 to 300 bp that act on a promoter to increase its transcription. Examples including the SV40 enhancer on the late side of the replication origin bp 100 to 270, a cytomegalovirus early promoter enhancer, the polyoma enhancer on the late side of the replication origin, and adenovirus enhancers.

Generally, recombinant expression vectors will include origins of replication and selectable markers permitting transformation of the host cell, e.g., the ampicillin resistance gene of *E. coli* and *S. cerevisiae* TRP1 gene, and a promoter derived from a highly-expressed gene to direct transcription of a downstream structural sequence. Such promoters can be derived from operons encoding glycolytic enzymes such as 3-phosphoglycerate kinase (PGK), α-factor, acid phosphatase, or heat shock proteins, among others. The heterologous structural sequence is assembled in appropriate phase with translation initiation and termination sequences, and preferably, a leader sequence capable of directing secretion of translated protein into the periplasmic space or extracellular medium. Optionally, the heterologous sequence can encode a fusion protein including an N-terminal identification peptide imparting desired characteristics, e.g., stabilization or simplified purification of expressed recombinant product.

Useful expression vectors for bacterial use are constructed by inserting a structural DNA sequence encoding a desired protein together with suitable translation initiation and termination signals in operable reading phase with a functional promoter. The vector will comprise one or more phenotypic selectable markers and an origin of replication to ensure maintenance of the vector and to, if desirable, provide amplification within the host. Suitable prokaryotic hosts for transformation include *E. coli, Bacillus subtilis, Salmonella typhimurium* and various species within the genera Pseudomonas, Streptomyces, and Staphylococcus, although others may also be employed as a matter of choice.

As a representative but nonlimiting example, useful expression vectors for bacterial use can comprise a selectable marker and bacterial origin of replication derived from commercially available plasmids comprising genetic elements of the well known cloning vector pBR322 (ATCC 37017). Such commercial vectors include, for example, pKK223-3 (Pharmacia Fine Chemicals, Uppsala, Sweden) and GEM1 (Promega Biotec, Madison, Wis., USA). These pBR322 "backbone" sections are combined with an appropriate promoter and the structural sequence to be expressed.

Following transformation of a suitable host strain and growth of the host strain to an appropriate cell density, the selected promoter is induced by appropriate means (e.g., temperature shift or chemical induction) and cells are cultured for an additional period.

Cells are typically harvested by centrifugation, disrupted by physical or chemical means, and the resulting crude extract retained for further purification.

Microbial cells employed in expression of proteins can be disrupted by any convenient method, including freeze-thaw cycling, sonication, mechanical disruption, or use of cell lysing agents, such methods are well known to those skilled in the art.

Various mammalian cell culture systems can also be employed to express recombinant protein. Examples of mammalian expression systems include the COS-7 lines of monkey kidney fibroblasts, described by Gluzman, Cell, 23:175 (1981), and other cell lines capable of expressing a compatible vector, for example, the C127, 3T3, CHO, HeLa and BHK cell lines. Mammalian expression vectors will comprise an origin of replication, a suitable promoter and enhancer, and also any necessary ribosome binding sites, polyadenylation site, splice donor and acceptor sites, transcriptional termination sequences, and 5' flanking nontranscribed sequences. DNA sequences derived from the SV40 splice, and polyadenylation sites may be used to provide the required nontranscribed genetic elements.

The HPRT-2 polypeptides can be recovered and purified from recombinant cell cultures by methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Protein refolding steps can be used, as necessary, in completing configuration of the mature protein. Finally, high performance liquid chromatography (HPLC) can be employed for final purification steps.

The polypeptides of the present invention may be a naturally purified product, or a product of chemical synthetic procedures, or produced by recombinant techniques from a prokaryotic or eukaryotic host (for example, by bacterial, yeast, higher plant, insect and mammalian cells in culture). Depending upon the host employed in a recombinant production procedure, the polypeptides of the present invention may be glycosylated or may be non-glycosylated. Polypeptides of the invention may also include an initial methionine amino acid residue.

The HPRT-2 polypeptides of the present invention catalyze the conversion of free purines into the corresponding purine nucleoside 5'-phosphates for biological re-use. Accordingly, the HPRT-2 polypeptide of the present invention may be employed to salvage purines and prevent the formation of uric acid.

The HPRT-2 polypeptides may be used to prevent or treat Lesch-Nyhan syndrome which is characterized by severe retardation, hyperuricemia, and severe neurological dysfunction. Lesch-Nyhan syndrome is an X-linked disorder characterized by mental retardation and bizarre behavior including self-mutilation.

The HPRT-2 polypeptides may also be used to treat kidney stones, renal failure (nephropathy), uricaciduria, precocious gout, anemia and nephrolithiasis, all of which are characterized by low levels of purines and excessive levels of uric acid.

This invention provides a method of screening compounds to identify antagonists which block the action of HPRT-2. An example of such an assay includes preparing an incubation mixture of 10 mM Tris-HCl (pH 7.4), 5 mM $MgCl_2$, 1 mM PRPP (Sigma Chemical Co., St. Louis, Mo.) and 20 $\mu$M [$^{14}$C]hypoxanthine (Amersham Corp.). Reactions are initiated by addition of approximately 10 $\mu$g of bacterial protein lysate from the TOP10 *E. Coli* cells transformed with the pTrcHIS(A) containing the HPRT-2 protein, and 50 $\mu$l aliquots were harvested at time intervals up to 1 hour and spotted on DE81 filter discs (Whatman Paper, Ltd., Maidstone, England) which bind IMP but not hypoxanthine. The filter discs are allowed to dry at room-temperature for 5 minutes and are subsequently washed in 1 liter of distilled water for 15 minutes, followed by 1 liter of 1 mM ammonium formate for 15 minutes, and a final wash in 1 liter of distilled water for 15 minutes. The filter discs are dehydrated in 70% ethanol, air-dried, and counted in a liquid scintillation counter. All assays are performed within the linear kinetic range with respect to protein concentration, stability, and time (Iovannisci, D. M. et al., J. Biol. Chem., 259:14617–14623 (1984).

HPRT-2 catalyzes the formation of [$^{14}$C]IMP. Once the level of activity of HPRT-2 is established as a control, the assay may be performed again, however, this time the potential compounds are added and the level of [$^{14}$C]IMP formation can be compared to the control to determine if the compound interferes with the action of HPRT-2 and is an antagonist.

Potential HPRT-2 antagonists include an antibody, or in some cases, an oligonucleotide, which binds to HPRT-2 and prevents its interaction with free purines to further prevent the conversion of the free purines into IMP and GMP.

Another potential HPRT-2 antagonist includes an antisense construct prepared using antisense technology which reduces the number of HPRT-2 molecules in circulation. Antisense technology can be used to control gene expression through triple-helix formation or antisense DNA or RNA, both of which methods are based on binding of a polynucleotide to DNA or RNA. For example, the 5' coding portion of the polynucleotide sequence, which encodes for the mature polypeptides of the present invention, is used to design an antisense RNA oligonucleotide of from about 10 to 40 base pairs in length. A DNA oligonucleotide is designed to be complementary to a region of the gene involved in transcription (triple helix—see Lee et al., Nucl. Acids Res., 6:3073 (1979); Cooney et al, Science, 241:456 (1988); and Dervan et al., Science, 251: 1360 (1991)), thereby preventing transcription and the production of HPRT-2. The antisense RNA oligonucleotide hybridizes to the mRNA in vivo and blocks translation of the mRNA molecule into the HPRT-2 (Antisense—Okano, J. Neurochem., 56:560 (1991); Oligodeoxynucleotides as Antisense Inhibitors of Gene Expression, CRC Press, Boca Raton, Fla. (1988)). The oligonucleotides described above can also be delivered to cells such that the antisense RNA or DNA may be expressed in vivo to inhibit production of HPRT-2.

HPRT-2 antagonists also include a mutated form, e.g. a negative dominant mutant, of HPRT-2 which interacts with xanthine and hypoxanthine but does not catalyze the conversion of a phosphoribosyl group to form IMP or GMP.

Potential HPRT-2 antagonists also include a small molecule which binds to and occupies the catalytic site of the HPRT-2 protein thereby making the catalytic site inaccessible to free purines such that conversion of the free purines into purine nucleoside 5'-phosphates is prevented. Examples of small molecules include but are not limited to small peptides or peptide-like molecules.

The antagonists may be employed to treat psoriasis, myxedema, hypo- and hyperparathyroidism, hypertension, myocardial infarction, advanced primary renal diseases, obesity, Down's syndrome, proliferative hematopoietic diseases, gout, and African sleeping sickness, since inhibiting the HPRT-2 enzyme arrests the growth and propagation of protozoan organisms such as *Trypanosoma brucei,* which is the cause of African sleeping sickness. All the above abnormalities, with the exception of African sleeping sickness, are related to an overabundance of purine synthesis. The antagonists may be employed in a composition with a pharmaceutically acceptable carrier, e.g., as hereinafter described.

The HPRT-2 polypeptides and antagonists may be employed in combination with a suitable pharmaceutical carrier. Such compositions comprise a therapeutically effective amount of the polypeptide or antagonist, and a pharmaceutically acceptable carrier or excipient. Such a carrier includes but is not limited to saline, buffered saline, dextrose, water, glycerol, ethanol, and combinations thereof. The formulation should suit the mode of administration.

The invention also provides a pharmaceutical pack or kit comprising one or more containers filled with one or more of the ingredients of the pharmaceutical compositions of the invention. Associated with such container(s) can be a notice in the form prescribed by a governmental agency regulating the manufacture, use or sale of pharmaceuticals or biological products, which notice reflects approval by the agency of manufacture, use or sale for human administration. In addition, the polypeptides and antagonists of the present invention may be employed in conjunction with other therapeutic compounds.

The pharmaceutical compositions may be administered in a convenient manner such as by the topical, intravenous, intraperitoneal, intramuscular, subcutaneous, intranasal or intradermal routes. The pharmaceutical compositions are administered in an amount which is effective for treating and/or prophylaxis of the specific indication. In general, the pharmaceutical compositions will be administered in an amount of at least about 10 $\mu$g/kg body weight and in most cases they will be administered in an amount not in excess of about 8 mg/Kg body weight per day. In most cases, the dosage is from about 10 $\mu$g/kg to about 1 mg/kg body weight daily, taking into account the routes of administration, symptoms, etc.

The HPRT-2 polypeptides and antagonists which are polypeptides may also be employed in accordance with the present invention by expression of such polypeptides in vivo, which is often referred to as "gene therapy."

Thus, for example, cells from a patient may be engineered with a polynucleotide (DNA or RNA) encoding a polypeptide ex vivo, with the engineered cells then being provided to a patient to be treated with the polypeptide. Such methods are well-known in the art. For example, cells may be engineered by procedures known in the art by use of a retroviral particle containing RNA encoding a polypeptide of the present invention.

Similarly, cells may be engineered in vivo for expression of a polypeptide in vivo by, for example, procedures known in the art. As known in the art, a producer cell for producing a retroviral particle containing RNA encoding the polypeptide of the present invention may be administered to a patient for engineering cells in vivo and expression of the polypeptide in vivo. These and other methods for administering a polypeptide of the present invention by such method should be apparent to those skilled in the art from the teachings of the present invention. For example, the expression vehicle for engineering cells may be other than a retrovirus, for example, an adenovirus which may be used to engineer cells in vivo after combination with a suitable delivery vehicle.

Retroviruses from which the retroviral plasmid vectors hereinabove mentioned may be derived include, but are not limited to, Moloney Murine Leukemia Virus, spleen necrosis virus, retroviruses such as Rous Sarcoma Virus, Harvey Sarcoma Virus, avian leukosis virus, gibbon ape leukemia virus, human immunodeficiency virus, adenovirus, Myeloproliferative Sarcoma Virus, and mammary tumor virus. In one embodiment, the retroviral plasmid vector is derived from Moloney Murine Leukemia Virus.

The vector includes one or more promoters. Suitable promoters which may be employed include, but are not limited to, the retroviral LTR; the SV40 promoter; and the human cytomegalovirus (CMV) promoter described in Miller, et al., *Biotechniques,* Vol. 7, No. 9, 980–990 (1989), or any other promoter (e.g., cellular promoters such as eukaryotic cellular promoters including, but not limited to, the histone, pol III, and β-actin promoters). Other viral promoters which may be employed include, but are not limited to, adenovirus promoters, thymidine kinase (TK) promoters, and B19 parvovirus promoters. The selection of a suitable promoter will be apparent to those skilled in the art from the teachings contained herein.

The nucleic acid sequence encoding the polypeptide of the present invention is under the control of a suitable promoter. Suitable promoters which may be employed include, but are not limited to, adenoviral promoters, such as the adenoviral major late promoter; or heterologous promoters, such as the cytomegalovirus (CMV) promoter; the respiratory syncytial virus (RSV) promoter; inducible promoters, such as the MMT promoter, the metallothionein promoter; heat shock promoters; the albumin promoter; the ApoAI promoter; human globin promoters; viral thymidine kinase promoters, such as the Herpes Simplex thymidine kinase promoter; retroviral LTRs (including the modified retroviral LTRs hereinabove described); the β-actin promoter; and human growth hormone promoters. The promoter also may be the native promoter which controls the gene encoding the polypeptide.

The retroviral plasmid vector is employed to transduce packaging cell lines to form producer cell lines. Examples of packaging cells which may be transfected include, but are not limited to, the PE501, PA317, ψ-2, ψ-AM, PA12, T19-14X, VT-19-17-H2, ψCRE, ψCRIP, GP+E-86, GP+envAm12, and DAN cell lines as described in Miller, *Human Gene Therapy,* Vol. 1, pgs. 5–14 (1990), which is incorporated herein by reference in its entirety. The vector may transduce the packaging cells through any means known in the art. Such means include, but are not limited to, electroporation, the use of liposomes, and $CaPO_4$ precipitation. In one alternative, the retroviral plasmid vector may be encapsulated into a liposome, or coupled to a lipid, and then administered to a host.

The producer cell line generates infectious retroviral vector particles which include the nucleic acid sequence(s) encoding the polypeptides. Such retroviral vector particles then may be employed, to transduce eukaryotic cells, either in vitro or in vivo. The transduced eukaryotic cells will express the nucleic acid sequence(s) encoding the polypeptide. Eukaryotic cells which may be transduced include, but are not limited to, embryonic stem cells, embryonic carcinoma cells, as well as hematopoietic stem cells, hepatocytes, fibroblasts, myoblasts, keratinocytes, endothelial cells, and bronchial epithelial cells.

This invention is also related to the use of the gene of the present invention as a diagnostic. Detection of a mutated form of the gene will allow a diagnosis of or a susceptibility to excessive uric acid formation and resultant Lesch-Nyhan Syndrome.

Individuals carrying mutations in the gene of the present invention may be detected at the DNA level by a variety of techniques. Nucleic acids for diagnosis may be obtained from a patient's cells, including but not limited to blood, urine, saliva, tissue biopsy and autopsy material. The genomic DNA may be used directly for detection or may be amplified enzymatically by using PCR (Saiki et al; Nature, 324:163–166 (1986)) prior to analysis. RNA or cDNA may also be used for the same purpose. As an example, PCR primers complementary to the nucleic acid encoding HPRT-2 can be used to identify and analyze mutations. For example, deletions and insertions can be detected by a change in size of the amplified product in comparison to the normal genotype. Point mutations can be identified by hybridizing amplified DNA to radiolabeled RNA or alternatively, radiolabeled antisense DNA sequences. Perfectly matched sequences can be distinguished from mismatched duplexes by RNase A digestion or by differences in melting temperatures.

Sequence differences between the reference gene and genes having mutations may be revealed by the direct DNA sequencing method. In addition, cloned DNA segments may be employed as probes to detect specific DNA segments. The sensitivity of this method is greatly enhanced when combined with PCR. For example, a sequencing primer is used with double-stranded PCR product or a single-stranded template molecule generated by a modified PCR. The sequence determination is performed by conventional procedures with radiolabeled nucleotide or by automatic sequencing procedures with fluorescent-tags.

Genetic testing based on DNA sequence differences may be achieved by detection of alteration in electrophoretic mobility of DNA fragments in gels with or without denaturing agents. Small sequence deletions and insertions can be visualized by high resolution gel electrophoresis. DNA fragments of different sequences may be distinguished on denaturing formamide gradient gels in which the mobilities of different DNA fragments are retarded in the gel at different positions according to their specific melting or partial melting temperatures (see, e.g., Myers et al., Science, 230:1242 (1985)).

Sequence changes at specific locations may also be revealed by nuclease protection assays, such as RNase and S1 protection or the chemical cleavage method (e.g., Cotton et al., PNAS, USA, 85:4397–4401 (1985)).

Thus, the detection of a specific DNA sequence may be achieved by methods such as hybridization, RNase protection, chemical cleavage, direct DNA sequencing or the use of restriction enzymes, (e.g., Restriction Fragment Length Polymorphisms (RFLP)) and Southern blotting of genomic DNA.

In addition to more conventional gel-electrophoresis and DNA sequencing, mutations can also be detected by in situ analysis.

The present invention also relates to a diagnostic assay for detecting altered levels of the polypeptide of the present invention in various tissues since an over-expression of the proteins compared to normal control tissue samples can detect the presence of HPRT-2. Assays used to detect levels of the polypeptide of the present invention in a sample derived from a host are well-known to those of skill in the art and include radioimmunoassays, competitive-binding assays, Western Blot analysis and preferably an ELISA assay. An ELISA assay initially comprises preparing an antibody specific to the HPRT-2 antigen, preferably a monoclonal antibody. In addition a reporter antibody is prepared against the monoclonal antibody. To the reporter antibody is attached a detectable reagent such as radioactivity, fluorescence or in this example a horseradish peroxidase enzyme. A sample is now removed from a host and incubated on a solid support, e.g. a polystyrene dish, that binds the proteins in the sample. Any free protein binding sites on the dish are then covered by incubating with a non-specific protein such as bovine serum albumin. Next, the monoclonal antibody is incubated in the dish during which time the monoclonal antibodies attached to any of the polypeptide of the present invention attached to the polystyrene dish. All unbound monoclonal antibody is washed out with buffer. The reporter antibody linked to horseradish peroxidase is now placed in the dish resulting in binding of the reporter antibody to any monoclonal antibody bound to the polypeptide of the present invention. Unattached reporter antibody is then washed out. Peroxidase substrates are then added to the dish and the amount of color developed in a given time period is a measurement of the amount of the polypeptide of the present invention present in a given volume of patient sample when compared against a standard curve.

A competition assay may be employed wherein antibodies specific to the polypeptide of the present invention are attached to a solid support and labeled HPRT-2 and a sample derived from the host are passed over the solid support and the amount of label detected attached to the solid support can be correlated to a quantity of the polypeptide of the present invention in the sample.

The sequences of the present invention are also valuable for chromosome identification. The sequence is specifically targeted to and can hybridize with a particular location on an individual human chromosome. Moreover, there is a current need for identifying particular sites on the chromosome. Few chromosome marking reagents based on actual sequence data (repeat polymorphisms) are presently available for marking chromosomal location. The mapping of DNAs to chromosomes according to the present invention is an important first step in correlating those sequences with genes associated with disease.

Briefly, sequences can be mapped to chromosomes by preparing PCR primers (preferably 15–25 bp) from the cDNA. Computer analysis of the 3' untranslated region of the gene is used to rapidly select primers that do not span more than one exon in the genomic DNA, thus complicating the amplification process. These primers are then used for PCR screening of somatic cell hybrids containing individual human chromosomes. Only those hybrids containing the human gene corresponding to the primer will yield an amplified fragment.

PCR mapping of somatic cell hybrids is a rapid procedure for assigning a particular DNA to a particular chromosome. Using the present invention with the same oligonucleotide primers, sublocalization can be achieved with panels of fragments from specific chromosomes or pools of large genomic clones in an analogous manner. Other mapping strategies that can similarly be used to map to its chromosome include in situ hybridization, prescreening with labeled flow-sorted chromosomes and preselection by hybridization to construct chromosome specific-cDNA libraries.

Fluorescence in situ hybridization (FISH) of a cDNA clone to a metaphase chromosomal spread can be used to provide a precise chromosomal location in one step. This technique can be used with cDNA having at least 50 or 60 bases. For a review of this technique, see Verma et al., Human Chromosomes: a Manual of Basic Techniques, Pergamon Press, New York (1988).

Once a sequence has been mapped to a precise chromosomal location, the physical position of the sequence on the chromosome can be correlated with genetic map data. Such data are found, for example, in V. McKusick, Mendelian Inheritance in Man (available on line through Johns Hopkins University Welch Medical Library). The relationship between genes and diseases that have been mapped to the same chromosomal region are then identified through linkage analysis (coinheritance of physically adjacent genes).

Next, it is necessary to determine the differences in the cDNA or genomic sequence between affected and unaffected individuals. If a mutation is observed in some or all of the affected individuals but not in any normal individuals, then the mutation is likely to be the causative agent of the disease.

With current resolution of physical mapping and genetic mapping techniques, a cDNA precisely localized to a chromosomal region associated with the disease could be one of between 50 and 500 potential causative genes. (This assumes 1 megabase mapping resolution and one gene per 20 kb).

The polypeptides, their fragments or other derivatives, or analogs thereof, or cells expressing them can be used as an immunogen to produce antibodies thereto. These antibodies can be, for example, polyclonal or monoclonal antibodies. The present invention also includes chimeric, single chain, and humanized antibodies, as well as Fab fragments, or the product of an Fab expression library. Various procedures known in the art may be used for the production of such antibodies and fragments.

Antibodies generated against the polypeptides corresponding to a sequence of the present invention can be obtained by direct injection of the polypeptides into an animal or by administering the polypeptides to an animal, preferably a nonhuman. The antibody so obtained will then bind the polypeptides itself. In this manner, even a sequence encoding only a fragment of the polypeptides can be used to generate antibodies binding the whole native polypeptides. Such antibodies can then be used to isolate the polypeptide from tissue expressing that polypeptide.

For preparation of monoclonal antibodies, any technique which provides antibodies produced by continuous cell line cultures can be used. Examples include the hybridoma technique (Kohler and Milstein, 1975, Nature, 256:495–497), the trioma technique, the human B-cell hybridoma technique (Kozbor et al., 1983, Immunology Today 4:72), and the EBV-hybridoma technique to produce human monoclonal antibodies (Cole, et al., 1985, in Monoclonal Antibodies and Cancer Therapy, Alan R. Liss, Inc., pp. 77–96).

Techniques described for the production of single chain antibodies (U.S. Pat. No. 4,946,778) can be adapted to produce single chain antibodies to immunogenic polypeptide products of this invention. Also, transgenic mice may be used to express humanized antibodies to immunogenic polypeptide products of this invention.

The present invention will be further described with reference to the following examples; however, it is to be understood that the present invention is not limited to such examples. All parts or amounts, unless otherwise specified, are by weight.

In order to facilitate understanding of the following examples certain frequently occurring methods and/or terms will be described.

"Plasmids" are designated by a lower case p preceded and/or followed by capital letters and/or numbers. The starting plasmids herein are either commercially available, publicly available on an unrestricted basis, or can be constructed from available plasmids in accord with published procedures. In addition, equivalent plasmids to those described are known in the art and will be apparent to the ordinarily skilled artisan.

"Digestion" of DNA refers to catalytic cleavage of the DNA with a restriction enzyme that acts only at certain sequences in the DNA. The various restriction enzymes used herein are commercially available and their reaction conditions, cofactors and other requirements were used as would be known to the ordinarily skilled artisan. For analytical purposes, typically 1 μg of plasmid or DNA fragment is used with about 2 units of enzyme in about 20 μl of buffer solution. For the purpose of isolating DNA fragments for plasmid construction, typically 5 to 50 μg of DNA are digested with 20 to 250 units of enzyme in a larger volume. Appropriate buffers and substrate amounts for particular restriction enzymes are specified by the manufacturer. Incubation times of about 1 hour at 37° C. are ordinarily used, but may vary in accordance with the supplier's instructions. After digestion the reaction is electrophoresed directly on a polyacrylamide gel to isolate the desired fragment.

Size separation of the cleaved fragments is performed using 8 percent polyacrylamide gel described by Goeddel, D. et al., Nucleic Acids Res., 8:4057 (1980).

"Oligonucleotides" refers to either a single stranded polydeoxynucleotide or two complementary polydeoxynucleotide strands which may be chemically synthesized. Such synthetic oligonucleotides have no 5' phosphate and thus will not ligate to another oligonucleotide without adding a phosphate with an ATP in the presence of a kinase. A synthetic oligonucleotide will ligate to a fragment that has not been dephosphorylated.

"Ligation" refers to the process of forming phosphodiester bonds between two double stranded nucleic acid fragments (Maniatis, T., et al., Id., p. 146). Unless otherwise provided, ligation may be accomplished using known buffers and conditions with 10 units to T4 DNA ligase ("ligase") per 0.5 μg of approximately equimolar amounts of the DNA fragments to be ligated.

Unless otherwise stated, transformation was performed as described in the method of Graham, F. and Van der Eb, A., Virology, 52:456–457 (1973).

EXAMPLE 1

Bacterial Expression and Purification of HPRT-2

Isolation of the full-length cDNA clone of HPRT-2 was completed by nested RACE-PCR of the fetal lung library to amplify the 5' end. Verification was done by sequence analysis and the full-length cDNA product encoding HPRT-2 was ligated into the Bam HI to Xho I site of pTrcHIS(A) (Invitrogen Corp., San Diego, Calif.) and transformed into TOP10 *E. Coli* (Invitrogen Corp., San Diego, Calif.) as prescribed by the vendor. Ampicillin resistant clones were selected and grown in TB media containing 100 μg/ml ampicillin as 250 ml cultures in the presence or absence of 1 mM isopropylthiogalactoside (IPTG). Cultures were harvested approximately two hours or until the OD=1.0. Protein extracts were prepared by successive freezing and thawing in 20 mM sodium phosphate (pH 7.4) buffer in the presence of 100 μM PMSF to inhibit proteolysis. Total protein concentrations were determined using the micro-BioRad protein assay (Hercules, Calif.). After clarification, solubilized HPRT-2 was purified by chromatography on a Nickel-chelate column under conditions that allow for type binding by proteins containing the 6-His tag (Hochuli, E., et al., J. Chromatography, 411:177–184 (1984)). HPRT-2 (95% pure) was eluted from the column in 6 molar guanidine HC1 pH 5.0, and for the purpose of renaturation, adjusted to 3 molar guanidine HC1, 100 mM sodium phosphate, 10 mM glutathione (reduced) and 2 mM glutathione (oxidized). After incubation in this solution for 12 hours, the protein was dialyzed against 10 mM sodium phosphate. The protein was then resolved by electrophoresis on a 12% SDS polyacrylamide gel.

EXAMPLE 2

Expression of Recombinant HPRT-2 in COS Cells

The expression of plasmid, HPRT-2 HA is derived from a vector pcDNAI/Amp (Invitrogen) containing: 1) SV40 origin of replication, 2) ampicillin resistance gene, 3) *E. coli* replication origin, 4) CMV promoter followed by a polylinker region, a SV40 intron and polyadenylation site. A DNA fragment encoding the entire HPRT-2 precursor and a HA tag fused in frame to its 3' end was cloned into the polylinker region of the vector, therefore, the recombinant protein expression is directed under the CMV promoter. The HA tag correspond to an epitope derived from the influenza hemagglutinin protein as previously described (I. Wilson, H. Niman, R. Heighten, A Cherenson, M. Connolly, and R. Lerner, 1984, Cell 37, 767). The infusion of HA tag to the target protein allows easy detection of the recombinant protein with an antibody that recognizes the HA epitope.

The plasmid construction strategy is described as follows:

The DNA sequence encoding for HPRT-2, ATCC # 75844, was constructed by PCR on the original EST cloned using two primers: the 5' primer sequence 5' TCCGTTATGGCGACCCGCAGCCCTGGCGTCGTGATTA 3' (SEQ ID NO:3) and the 3' primer sequence 5' CATCAATGAGCACGGGTAAAG 3' (SEQ ID NO:4). The PCR amplified DNA fragment and the vector, pcDNAP/Amp, were digested with BamHI and XhoI restriction enzyme and ligated. The ligation mixture was transformed into *E. coli* strain SURE (available from Stratagene Cloning Systems, 11099 North Torrey Pines Road, La Jolla, Calif. 92037) the transformed culture was plated on ampicillin media plates and resistant colonies were selected. Plasmid DNA was isolated from transformants and examined by restriction analysis for the presence of the correct fragment. For expression of the recombinant HPRT-2, COS cells were transfected with the expression vector by DEAE-DEXTRAN method. (J. Sambrook, E. Fritsch, T. Maniatis, Molecular Cloning: A Laboratory Manual, Cold Spring Laboratory Press, (1989)). The expression of the HPRT-2 HA protein was detected by radiolabeling and immunoprecipitation method. (E. Harlow, D. Lane, Antibodies: A Laboratory Manual, Cold Spring Harbor Laboratory Press, (1988)). Cells were labeled for 8 hours with $^{35}$S-cysteine two days post transfection. Culture media were then collected and cells were lysed with detergent (RIPA buffer (150 mM NaCl, 1% NP-40, 0.1% SDS, 1% NP-40, 0.5% DOC, 50 mM Tris, pH 7.5). (Wilson, I. et al., Id. 37:767 (1984)). Both cell lysate and culture media were precipitated with a HA specific monoclonal antibody. Proteins precipitated were analyzed on 15% SDS-PAGE gels.

EXAMPLE 3

Cloning and Expression of HPRT-2 Using the Baculovirus Expression System

The DNA sequence encoding the full length HPRT-2 protein, ATCC # 75844, was amplified using PCR oligonucleotide primers corresponding to the 5' and 3' sequences of the gene:

The 5' primer has the sequence 5' GATCGGAGACTACGGGCGAATGGC 3' (SEQ ID NO:5) and the 3' primer has the sequence 5' CAGGTGCATCAATGAGCACGGGTAAAG 3' (SEQ ID NO:6). The amplified sequences were isolated from a 1% agarose gel using a commercially available kit ("Geneclean," BIO 101 Inc., La Jolla, Calif.). The fragment was then digested with the endonucleases BamHI and XhoI and then purified also on a 1% agarose gel. This fragment is designated F2.

The vector pRG1 (modification of pVL941 vector, discussed below) is used for the expression of the HPRT-2 protein using the baculovirus expression system (for review see: Summers, M. D. and Smith, G. E. 1987, A manual of methods for baculovirus vectors and insect cell culture procedures, Texas Agricultural Experimental Station Bulletin No. 1555). This expression vector contains the strong polyhedrin promoter of the Autographa californica nuclear polyhedrosis virus (AcMNPV) followed by the recognition sites for the restriction endonucleases BamHI and XhoI. The polyadenylation site of the simian virus (SV)40 is used for efficient polyadenylation. For an easy selection of recombinant viruses the beta-galactosidase gene from *E. coli* is inserted in the same orientation as the polyhedrin promoter followed by the polyadenylation signal of the polyhedrin gene. The polyhedrin sequences are flanked at both sides by viral sequences for the cell-mediated homologous recombination of cotransfected wild-type viral DNA. Many other baculovirus vectors could be used in place of pRG1 such as pAc373, pVL941 and pAcIM1 (Luckow, V. A. and Summers, M. D., Virology, 170:31–39).

The plasmid was digested with the restriction enzymes BamHI and XhoI and then dephosphorylated using calf intestinal phosphatase by procedures known in the art. The DNA was then isolated from a 1% agarose gel. This vector DNA is designated V2.

Fragment F2 and the dephosphorylated plasmid V2 were ligated with T4 DNA ligase. *E. coli* HB101 cells were then transformed and bacteria identified that contained the plasmid (pBacHPRT-2) with the HPRT-2 gene using the enzymes BamHI and XhoI. The sequence of the cloned fragment was confirmed by DNA sequencing.

5 $\mu$g of the plasmid pBacHPRT-2 were cotransfected with 1.0 $\mu$g of a commercially available linearized baculovirus ("BaculoGold™ baculovirus DNA", Pharmingen, San Diego, Calif.) using the lipofection method (Felgner et al. Proc. Natl. Acad. Sci. USA, 84:7413–7417 (1987)).

1 $\mu$g of BaculoGold™ virus DNA and 5 $\mu$g of the plasmid pBacHPRT-2 were mixed in a sterile well of a microtiter plate containing 50 $\mu$l of serum free Grace's medium (Life Technologies Inc., Gaithersburg, Md.). Afterwards 10, $\mu$l Lipofectin plus 90 $\mu$l Grace's medium were added, mixed and incubated for 15 minutes at room temperature. Then the transfection mixture was added dropwise to the Sf9 insect cells (ATCC CRL 1711) seeded in a 35 mm tissue culture plate with 1 ml Grace's medium without serum. The plate was rocked back and forth to mix the newly added solution. The plate was then incubated for 5 hours at 27° C. After 5 hours the transfection solution was removed from the plate and 1 ml of Grace's insect medium supplemented with 10% fetal calf serum was added. The plate was put back into an incubator and cultivation continued at 27° C. for four days.

After four days the supernatant was collected and a plaque assay performed similar as described by Summers and Smith (supra). As a modification an agarose gel with "Blue Gal" (Life Technologies Inc., Gaithersburg) was used which allows an easy isolation of blue stained plaques. (A detailed description of a "plaque assay" can also be found in the user's guide for insect cell culture and baculovirology distributed by Life Technologies Inc., Gaithersburg, page 9–10).

Four days after the serial dilution of the viruses was added to the cells, blue stained plaques were picked with the tip of an Eppendorf pipette. The agar containing the recombinant viruses was then resuspended in an Eppendorf tube containing 200 $\mu$l of Grace's medium. The agar was removed by a brief centrifugation and the supernatant containing the recombinant baculovirus was used to infect Sf9 cells seeded in 35 mm dishes. Four days later the supernatants of these culture dishes were harvested and then stored at 4° C.

Sf9 cells were grown in Grace's medium supplemented with 10% heat-inactivated FBS. The cells were infected with the recombinant baculovirus V-HPRT-2 at a multiplicity of infection (MOI) of 2. Six hours later the medium was removed and replaced with SF900 II medium minus methionine and cysteine (Life Technologies Inc., Gaithersburg). 42 hours later 5 $\mu$Ci of $^{35}$S-methionine and 5 $\mu$Ci $^{35}$S cysteine (Amersham) were added. The cells were further incubated for 16 hours before they were harvested by centrifugation and the labeled proteins visualized by SDS-PAGE and autoradiography.

EXAMPLE 4

Expression via Gene Therapy

Fibroblasts are obtained from a subject by skin biopsy. The resulting tissue is placed in tissue-culture medium and separated into small pieces. Small chunks of the tissue are placed on a wet surface of a tissue culture flask, approximately ten pieces are placed in each flask. The flask is turned upside down, closed tight and left at room temperature over night. After 24 hours at room temperature, the flask is inverted and the chunks of tissue remain fixed to the bottom of the flask and fresh media (e.g., Ham's F12 media, with 10% FBS, penicillin and streptomycin, is added. This is then incubated at 37° C. for approximately one week. At this time, fresh media is added and subsequently changed every several days. After an additional two weeks in culture, a monolayer of fibroblasts emerge. The monolayer is trypsinized and scaled into larger flasks.

pMV-7 (Kirschmeier, P. T. et al, DNA, 7:219–25 (1988) flanked by the long terminal repeats of the Moloney murine sarcoma virus, is digested with EcoRI and HindIII and subsequently treated with calf intestinal phosphatase. The linear vector is fractionated on agarose gel and purified, using glass beads.

The cDNA encoding a polypeptide of the present invention is amplified using PCR primers which correspond to the 5' and 3' end sequences respectively. The 5' primer containing an EcoRI site and the 3' primer further includes a HindIII site. Equal quantities of the Moloney murine sarcoma virus linear backbone and the amplified EcoRI and HindIII fragment are added together, in the presence of T4 DNA ligase. The resulting mixture is maintained under conditions appropriate for ligation of the two fragments. The ligation mixture is used to transform bacteria HB101, which are then plated onto agar-containing kanamycin for the purpose of confirming that the vector had the gene of interest properly inserted.

The amphotropic pA317 or GP+am12 packaging cells are grown in tissue culture to confluent density in Dulbecco's Modified Eagles Medium (DMEM) with 10% calf serum (CS), penicillin and streptomycin. The MSV vector containing the gene is then added to the media and the packaging cells are transduced with the vector. The packaging cells now produce infectious viral particles containing the gene (the packaging cells are now referred to as producer cells).

Fresh media is added to the transduced producer cells, and subsequently, the media is harvested from a 10 cm plate of confluent producer cells. The spent media, containing the infectious viral particles, is filtered through a millipore filter to remove detached producer cells and this media is then used to infect fibroblast cells. Media is removed from a sub-confluent plate of fibroblasts and quickly replaced with the media from the producer cells. This media is removed and replaced with fresh media. If the titer of virus is high, then virtually all fibroblasts will be infected and no selection is required. If the titer is very low, then it is necessary to use a retroviral vector that has a selectable marker, such as neo or his.

The engineered fibroblasts are then injected into the host, either alone or after having been grown to confluence on cytodex 3 microcarrier beads. The fibroblasts now produce the protein product.

Numerous modifications and variations of the present invention are possible in light of the above teachings and, therefore, within the scope of the appended claims, the invention may be practiced otherwise than as particularly described.

SEQUENCE LISTING

```
<160> NUMBER OF SEQ ID NOS: 11

<210> SEQ ID NO 1
<211> LENGTH: 1386
<212> TYPE: DNA
<213> ORGANISM: Homo sapiens
<220> FEATURE:
<221> NAME/KEY: CDS
<222> LOCATION: (626)..(1264)
<223> OTHER INFORMATION:

<400> SEQUENCE: 1

gatttttgt gatatcttct tcgggggggg ggggaaccta ttgtataaac gccaaccaac      60

cggccctttt ttgggtacct ggccatttta cttggcccat tttggtaaaa tgttcctttc    120

cctgcgttaa tccccctgat tccttgtggg ataacccgta ttcccccct tagagtgaat     180

ttgaaaaccc tttcgcccgg aaggggaccg accgagccca gcgattcatg gagcgaggaa    240

agcgggaaga gcgcccaata cccaagccgc ctctcgccgg cgcgttgtgc gattcattaa    300

tacagctgcc acgacaggtt tcccgactgg aaagcggtca gtgagcgcaa cacaattaat    360

gtgagttagc tcactcatta ggcaccccag gctttacact ttatgcttcc ggctcgtatg    420

ttgtgtggaa ttgtgagcgg ataacaattt cacacaggaa acagctatga ccatgattac    480

gtccaagctc gaaattaacc ctcactaaag ggaacaaaaa ctggagctcc accgcggtgg    540

cggccgctct agaactagtg gatcccccgg gctccaggaa ttcgccacga ccgggaggac    600

cgaggaggcg ccagactacg ggcga atg gcg acc cgc agc cct ggc gtc gtg      652
                            Met Ala Thr Arg Ser Pro Gly Val Val
                            1               5

att atg gat gat tgg cca ggg tat gac ttg aat tta ttc acg tac cca      700
Ile Met Asp Asp Trp Pro Gly Tyr Asp Leu Asn Leu Phe Thr Tyr Pro
10                  15                  20                  25

cag cac tat tat gga gac ttg gag tat gtc ctc atc cct cat ggt atc      748
Gln His Tyr Tyr Gly Asp Leu Glu Tyr Val Leu Ile Pro His Gly Ile
                30                  35                  40

att gtg gac aga att gag cgg ctg gcc aag gat att atg aaa gac ata      796
Ile Val Asp Arg Ile Glu Arg Leu Ala Lys Asp Ile Met Lys Asp Ile
            45                  50                  55

gga tat agt gac atc atg gtc ctg tgt gtg ctt aaa ggg ggg tac aaa      844
Gly Tyr Ser Asp Ile Met Val Leu Cys Val Leu Lys Gly Gly Tyr Lys
        60                  65                  70

ttc tgt gct gat ctc gta gaa cac ctt aag aac atc agc cga aat tca      892
Phe Cys Ala Asp Leu Val Glu His Leu Lys Asn Ile Ser Arg Asn Ser
    75                  80                  85

gat cgg ttt gtc tca atg aag gtt gat ttc atc aga cta aaa agt tac      940
Asp Arg Phe Val Ser Met Lys Val Asp Phe Ile Arg Leu Lys Ser Tyr
90                  95                  100                 105

agg aat gac cag tcc atg ggt gag atg cag ata atc gga ggc ggt gat      988
Arg Asn Asp Gln Ser Met Gly Glu Met Gln Ile Ile Gly Gly Gly Asp
                110                 115                 120

ctt tca acg ctg gct gga aag aat ttt ctc att gtt gag gat gtt gtc     1036
Leu Ser Thr Leu Ala Gly Lys Asn Phe Leu Ile Val Glu Asp Val Val
            125                 130                 135

gga act ggg agg acc atg aaa gca cta ctc agc aat ata gag aaa tac     1084
Gly Thr Gly Arg Thr Met Lys Ala Leu Leu Ser Asn Ile Glu Lys Tyr
        140                 145                 150

aag ccc aac atg att aag gta gcc agt ttg ttg gtg aag aga aca tcc     1132
Lys Pro Asn Met Ile Lys Val Ala Ser Leu Leu Val Lys Arg Thr Ser
    155                 160                 165
```

-continued

```
aga agt gac ggc ttt aga cct gac tat gct gga ttt gag att cca cac     1180
Arg Ser Asp Gly Phe Arg Pro Asp Tyr Ala Gly Phe Glu Ile Pro His
170                 175                 180                 185

tta ttt gtg gtg gga tat gcc tta gat tac aat gaa tac ttc aga gat     1228
Leu Phe Val Val Gly Tyr Ala Leu Asp Tyr Asn Glu Tyr Phe Arg Asp
                190                 195                 200

ctg aat cac ata tgc gtc atc aat gag cac ggg taa aggaaaatat         1274
Leu Asn His Ile Cys Val Ile Asn Glu His Gly
            205                 210

cgagtcttaa agacatgaat tctcaccact aaaggcccca gataggatca tttttacgcc   1334

tgtcttgggg agccagttgc aagttgggcc cccccggatc ttcatcagga gg           1386


<210> SEQ ID NO 2
<211> LENGTH: 212
<212> TYPE: PRT
<213> ORGANISM: Homo sapiens

<400> SEQUENCE: 2

Met Ala Thr Arg Ser Pro Gly Val Val Ile Met Asp Asp Trp Pro Gly
1               5                   10                  15

Tyr Asp Leu Asn Leu Phe Thr Tyr Pro Gln His Tyr Tyr Gly Asp Leu
            20                  25                  30

Glu Tyr Val Leu Ile Pro His Gly Ile Ile Val Asp Arg Ile Glu Arg
        35                  40                  45

Leu Ala Lys Asp Ile Met Lys Asp Ile Gly Tyr Ser Asp Ile Met Val
    50                  55                  60

Leu Cys Val Leu Lys Gly Gly Tyr Lys Phe Cys Ala Asp Leu Val Glu
65                  70                  75                  80

His Leu Lys Asn Ile Ser Arg Asn Ser Asp Arg Phe Val Ser Met Lys
                85                  90                  95

Val Asp Phe Ile Arg Leu Lys Ser Tyr Arg Asn Asp Gln Ser Met Gly
            100                 105                 110

Glu Met Gln Ile Ile Gly Gly Gly Asp Leu Ser Thr Leu Ala Gly Lys
        115                 120                 125

Asn Phe Leu Ile Val Glu Asp Val Val Gly Thr Gly Arg Thr Met Lys
    130                 135                 140

Ala Leu Leu Ser Asn Ile Glu Lys Tyr Lys Pro Asn Met Ile Lys Val
145                 150                 155                 160

Ala Ser Leu Leu Val Lys Arg Thr Ser Arg Ser Asp Gly Phe Arg Pro
                165                 170                 175

Asp Tyr Ala Gly Phe Glu Ile Pro His Leu Phe Val Val Gly Tyr Ala
            180                 185                 190

Leu Asp Tyr Asn Glu Tyr Phe Arg Asp Leu Asn His Ile Cys Val Ile
        195                 200                 205

Asn Glu His Gly
    210


<210> SEQ ID NO 3
<211> LENGTH: 37
<212> TYPE: DNA
<213> ORGANISM: Artificial Sequence
<220> FEATURE:
<223> OTHER INFORMATION: Primer for PCR

<400> SEQUENCE: 3

tccgttatgg cgacccgcag ccctggcgtc gtgatta                           37
```

<210> SEQ ID NO 4
<211> LENGTH: 21
<212> TYPE: DNA
<213> ORGANISM: Artificial Sequence
<220> FEATURE:
<223> OTHER INFORMATION: Primer for PCR

<400> SEQUENCE: 4
catcaatgag cacgggtaaa g 21

<210> SEQ ID NO 5
<211> LENGTH: 24
<212> TYPE: DNA
<213> ORGANISM: Artificial Sequence
<220> FEATURE:
<223> OTHER INFORMATION: Primer for PCR

<400> SEQUENCE: 5
gatcggagac tacgggcgaa tggc 24

<210> SEQ ID NO 6
<211> LENGTH: 27
<212> TYPE: DNA
<213> ORGANISM: Artificial Sequence
<220> FEATURE:
<223> OTHER INFORMATION: Primer for PCR

<400> SEQUENCE: 6
caggtgcatc aatgagcacg ggtaaag 27

<210> SEQ ID NO 7
<211> LENGTH: 218
<212> TYPE: PRT
<213> ORGANISM: Homo sapiens

<400> SEQUENCE: 7

```
Met Ala Thr Arg Ser Pro Gly Val Val Ile Ser Asp Asp Glu Pro Gly
1               5                   10                  15

Tyr Asp Leu Asp Leu Phe Cys Ile Pro Asn His Tyr Ala Glu Asp Leu
            20                  25                  30

Glu Arg Val Phe Ile Pro His Gly Leu Ile Met Asp Arg Thr Glu Arg
        35                  40                  45

Leu Ala Arg Asp Val Met Lys Glu Met Gly Gly His His Ile Val Ala
    50                  55                  60

Leu Cys Val Leu Lys Gly Gly Tyr Lys Phe Phe Ala Asp Leu Leu Asp
65                  70                  75                  80

Tyr Ile Lys Ala Leu Asn Arg Asn Ser Asp Arg Ser Ile Pro Met Thr
                85                  90                  95

Val Asp Phe Ile Arg Leu Lys Ser Tyr Cys Asn Asp Gln Ser Thr Gly
            100                 105                 110

Asp Ile Lys Val Ile Gly Gly Asp Asp Leu Ser Thr Leu Thr Gly Lys
        115                 120                 125

Asn Val Leu Ile Val Glu Asp Ile Ile Asp Thr Gly Lys Thr Met Gln
    130                 135                 140

Thr Leu Leu Ser Leu Val Arg Gln Tyr Asn Pro Lys Met Val Lys Val
145                 150                 155                 160

Ala Ser Leu Leu Val Lys Arg Thr Pro Arg Ser Val Gly Tyr Lys Pro
                165                 170                 175

Asp Phe Val Gly Phe Glu Ile Pro Asp Lys Phe Val Val Gly Tyr Ala
            180                 185                 190
```

```
Leu Asp Tyr Asn Glu Tyr Phe Arg Asp Leu Asn His Val Cys Val Ile
        195                 200                 205

Ser Glu Thr Gly Lys Ala Lys Tyr Lys Ala
    210                 215


<210> SEQ ID NO 8
<211> LENGTH: 218
<212> TYPE: PRT
<213> ORGANISM: Cricetulus longicaudatus

<400> SEQUENCE: 8

Met Ala Thr Arg Ser Pro Ser Val Val Ile Ser Asp Asp Glu Pro Gly
1               5                   10                  15

Tyr Asp Leu Asp Leu Phe Cys Ile Pro Asn His Tyr Val Glu Asp Leu
            20                  25                  30

Glu Lys Val Phe Ile Pro His Gly Val Ile Met Asp Arg Thr Glu Arg
        35                  40                  45

Leu Ala Arg Asp Val Met Lys Glu Met Gly Gly His His Ile Val Ala
    50                  55                  60

Leu Cys Val Leu Lys Gly Gly Tyr Lys Phe Phe Ala Asp Leu Leu Asp
65                  70                  75                  80

Tyr Ile Lys Ala Leu Asn Arg Asn Ser Asp Arg Ser Ile Pro Met Thr
                85                  90                  95

Val Asp Phe Ile Arg Leu Lys Ser Tyr Cys Asn Asp Gln Ser Thr Gly
            100                 105                 110

Asp Ile Lys Val Ile Gly Gly Asp Asp Leu Ser Thr Leu Thr Gly Lys
        115                 120                 125

Asn Val Leu Ile Val Glu Asp Ile Ile Asp Thr Gly Lys Thr Met Gln
    130                 135                 140

Thr Leu Leu Ser Leu Val Lys Arg Tyr Asn Pro Lys Met Val Lys Val
145                 150                 155                 160

Ala Ser Leu Leu Val Lys Arg Thr Ser Arg Ser Val Gly Tyr Arg Pro
                165                 170                 175

Asp Phe Val Gly Phe Glu Ile Pro Asp Lys Phe Val Val Gly Tyr Ala
            180                 185                 190

Leu Asp Tyr Asn Glu Tyr Phe Arg Asp Leu Asn His Ile Cys Val Ile
        195                 200                 205

Ser Glu Thr Gly Lys Ala Lys Tyr Lys Ala
    210                 215


<210> SEQ ID NO 9
<211> LENGTH: 231
<212> TYPE: PRT
<213> ORGANISM: Plasmodium falciparum

<400> SEQUENCE: 9

Met Pro Ile Pro Asn Asn Pro Gly Ala Gly Glu Asn Ala Phe Asp Pro
1               5                   10                  15

Val Phe Val Lys Asp Asp Asp Gly Tyr Asp Leu Asp Ser Phe Met Ile
            20                  25                  30

Pro Ala His Tyr Lys Lys Tyr Leu Thr Lys Val Leu Val Pro Asn Gly
        35                  40                  45

Val Ile Lys Asn Arg Ile Glu Lys Leu Ala Tyr Asp Ile Lys Lys Val
    50                  55                  60

Tyr Asn Asn Glu Glu Phe His Ile Leu Cys Leu Leu Lys Gly Ser Arg
65                  70                  75                  80
```

```
Gly Phe Phe Thr Ala Leu Leu Lys His Leu Ser Arg Ile His Asn Tyr
                85                  90                  95

Ser Ala Val Glu Met Ser Lys Pro Leu Phe Gly Glu His Tyr Val Arg
            100                 105                 110

Val Lys Ser Tyr Cys Asn Asp Gln Ser Thr Gly Thr Leu Glu Ile Val
        115                 120                 125

Ser Glu Asp Leu Ser Cys Leu Lys Gly Lys His Val Leu Ile Val Glu
    130                 135                 140

Asp Ile Ile Asp Thr Gly Lys Thr Leu Val Lys Phe Cys Glu Tyr Leu
145                 150                 155                 160

Lys Lys Phe Glu Ile Lys Thr Val Ala Ile Ala Cys Leu Phe Ile Lys
                165                 170                 175

Arg Thr Pro Leu Trp Asn Gly Phe Lys Ala Asp Phe Val Gly Phe Ser
            180                 185                 190

Ile Pro Asp His Phe Val Val Gly Tyr Ser Leu Asp Tyr Asn Glu Ile
        195                 200                 205

Phe Arg Asp Leu Asp His Cys Cys Leu Val Asn Asp Glu Gly Lys Lys
    210                 215                 220

Lys Tyr Lys Ala Thr Ser Leu
225                 230


<210> SEQ ID NO 10
<211> LENGTH: 210
<212> TYPE: PRT
<213> ORGANISM: Trypanosoma brucei

<400> SEQUENCE: 10

Met Glu Pro Ala Cys Lys Tyr Asp Phe Ala Thr Ser Val Leu Phe Thr
1               5                   10                  15

Glu Ala Glu Leu His Thr Arg Met Arg Gly Val Ala Gln Arg Ile Ala
            20                  25                  30

Asp Asp Tyr Ser Asn Cys Asn Leu Lys Pro Leu Glu Asn Pro Leu Val
        35                  40                  45

Ile Val Ser Val Leu Lys Gly Ser Phe Val Phe Thr Ala Asp Met Val
    50                  55                  60

Arg Ile Leu Gly Asp Phe Gly Val Pro Thr Arg Val Glu Phe Leu Arg
65                  70                  75                  80

Ala Ser Ser Tyr Gly His Asp Thr Lys Ser Cys Gly Arg Val Asp Val
                85                  90                  95

Lys Ala Asp Gly Leu Cys Asp Ile Arg Gly Lys His Val Leu Val Leu
            100                 105                 110

Glu Asp Ile Leu Asp Thr Ala Leu Thr Leu Arg Glu Val Val Asp Ser
        115                 120                 125

Leu Lys Lys Ser Glu Pro Ala Ser Ile Lys Thr Leu Val Ala Ile Asp
    130                 135                 140

Lys Pro Gly Gly Arg Lys Ile Pro Phe Thr Ala Glu Tyr Val Val Ala
145                 150                 155                 160

Asp Val Pro Asn Val Phe Val Val Gly Tyr Gly Leu Asp Tyr Asp Gln
                165                 170                 175

Ser Tyr Arg Glu Val Arg Asp Val Val Ile Leu Lys Pro Ser Val Tyr
            180                 185                 190

Glu Thr Trp Gly Lys Glu Leu Glu Arg Arg Lys Ala Ala Gly Glu Ala
        195                 200                 205

Lys Arg
```

-continued

```
210


<210> SEQ ID NO 11
<211> LENGTH: 5
<212> TYPE: PRT
<213> ORGANISM: Homo sapiens

<400> SEQUENCE: 11

Arg Lys Ile Ser Ser
1               5
```

What is claimed is:

1. An isolated nucleic acid molecule consisting of at least 50 contiguous nucleotides of nucleotides 626 to 1260 of SEQ ID NO:1, or the completely complementary strand thereto.

2. The isolated nucleic acid molecule of claim 1, wherein said nucleic acid molecule consists of at least 50 contiguous nucleotides of nucleotides 626 to 1260 of SEQ ID NO:1.

3. The isolated nucleic acid molecule of claim 1, wherein said nucleic acid molecule consists of at least 50 contiguous nucleotides of the completely complementary strand of nucleotides 626 to 1260 of SEQ ID NO:1.

4. An isolated nucleic acid molecule consisting of at least 50 contiguous nucleotides of nucleotides 626 to 1260 of SEQ ID NO: 1, or the completely complementary strand thereto, wherein said isolated nucleic acid is linked to a heterologous polynucleotide encoding a heterologous polypeptide.

5. A recombinant vector comprising the isolated nucleic acid molecule of claim 1.

6. The recombinant vector of claim 5, wherein said nucleic acid molecule is operably associated with a heterologous regulatory sequence that controls gene expression.

7. A recombinant host cell comprising the isolated nucleic acid molecule of claim 1.

8. The recombinant host cell of claim 7, wherein said nucleic acid molecule is operably associated with a heterologous regulatory sequence that controls gene expression.

9. A method for producing a polypeptide, comprising:

(a) culturing a host cell under conditions suitable to produce a polypeptide encoded by the nucleic acid molecule of claim 2; and (b) recovering the polypeptide from the cell culture.

10. An isolated nucleic acid molecule consisting of at least 50 contiguous nucleotides of the coding sequence of the human cDNA contained in ATCC Deposit No. 75844, or the completely complementary strand thereto.

11. The isolated nucleic acid molecule of claim 10, wherein said nucleic acid molecule consists of at least 50 contiguous nucleotides of the coding sequence of the human cDNA contained in ATCC Deposit No. 75844.

12. The isolated nucleic acid molecule of claim 10, wherein said nucleic acid molecule consists of at least 50 contiguous nucleotides of the completely complementary strand of the coding sequence of the human cDNA contained in ATCC Deposit No.75844.

13. An isolated nucleic acid molecule consisting of at least 50 contiguous nucleotides of the coding sequence of the human cDNA contained in ATCC Deposit No. 75844, or the completely complementary strand thereto, wherein said isolated nucleic acid is linked to a heterologous polynucleotide encoding a heterologous polypeptide.

14. A recombinant vector comprising the isolated nucleic acid molecule of claim 10.

15. The recombinant vector of claim 14, wherein said nucleic acid molecule is operably associated with a heterologous regulatory sequence that controls gene expression.

16. A recombinant host cell comprising the isolated nucleic acid molecule of claim 10.

17. The recombinant host cell of claim 16, wherein said nucleic acid molecule is operably associated with a heterologous regulatory sequence that controls gene expression.

18. A method for producing a polypeptide, comprising:

(a) culturing a host cell under conditions suitable to produce a polypeptide encoded by the nucleic acid molecule of claim 11; and (b) recovering the polypeptide from the cell culture.

19. An isolated nucleic acid molecule comprising a polynucleotide sequence encoding a polypeptide selected from the group consisting of:

(a) a polypeptide comprising amino acids 1 to 212 of SEQ ID NO:2;

(b) a polypeptide comprising amino acids 2 to 212 of SEQ ID NO:2;

(c) a polypeptide comprising an amino acid sequence of the full-length polypeptide encoded by the cDNA contained in ATCC Deposit No. 75844; and (d) a polypeptide comprising an amino acid sequence of the full-length polypeptide, excluding the N-terminal methionine, encoded by the cDNA contained in ATCC Deposit No. 75844.

20. The isolated nucleic acid molecule of claim 19, wherein said polynucleotide sequence encoding the polypeptide sequence is (a).

21. The isolated nucleic acid molecule of claim 19, wherein said polynucleotide sequence encoding the polypeptide sequence is (b).

22. The isolated nucleic acid molecule of claim 19, wherein said polynucleotide sequence encoding the polypeptide sequence is (c).

23. The isolated nucleic acid molecule of claim 19, wherein said polynucleotide sequence encoding the polypeptide sequence is (d).

24. The isolated nucleic acid molecule of claim 19, wherein said polynucleotide sequence comprises a heterologous polynucleotide sequence.

25. The isolated nucleic acid molecule of claim 24, wherein said heterologous polynucleotide sequence encodes a heterologous polypeptide sequence.

26. A recombinant vector comprising the isolated nucleic acid molecule of claim 19.

27. The recombinant vector of claim 26, wherein said nucleic acid molecule is operably associated with a heterologous regulatory sequence that controls gene expression.

28. A recombinant host cell comprising the isolated nucleic acid molecule of claim 19.

29. The recombinant host cell of claim 28, wherein said nucleic acid molecule is operably associated with a heterologous regulatory sequence that controls gene expression.

30. A method of producing a polypeptide, comprising:

(a) culturing a host cell under conditions suitable to produce a polypeptide encoded by the nucleic acid molecule of claim 19; and (b) recovering the polypeptide from the cell culture.

31. An isolated nucleic acid molecule consisting of a polynucleotide sequence encoding a polypeptide selected from the group consisting of:

(a) a polypeptide consisting of at least 30 contiguous amino acid residues of amino acids 1 to 212 of SEQ ID NO:2;

(b) a polypeptide consisting of at least 50 contiguous amino acid residues 1 to 212 of SEQ ID NO:2;

(c) a polypeptide consisting of at least 30 contiguous amino acid residues of the polypeptide encoded by the cDNA contained in ATCC Deposit No. 75844; and (d) a polypeptide consisting of at least 50 contiguous amino acid residues of the polypeptide encoded by the cDNA contained in ATCC Deposit No. 75844.

32. The isolated nucleic acid molecule of claim 31, wherein said polynucleotide sequence encoding the polypeptide sequence is (a).

33. The isolated nucleic acid molecule of claim 31, wherein said polynucleotide sequence encoding the polypeptide sequence is (b).

34. The isolated nucleic acid molecule of claim 31, wherein said polynucleotide sequence encoding the polypeptide sequence is (c).

35. The isolated nucleic acid molecule of claim 31, wherein said polynucleotide sequence encoding the polypeptide sequence is (d).

36. An isolated nucleic acid molecule consisting of a polynucleotide sequence encoding a polypeptide selected from the group consisting of:

(a) a polypeptide consisting of at least 30 contiguous amino acid residues of amino acids 1 to 212 of SEQ ID NO: 2;

(b) a polypeptide consisting of at least 50 contiguous amino acid residues of amino acids 1 to 212 of SEQ ID NO: 2;

(c) a polypeptide consisting of at least 30 contiguous amino acid residues of the polypeptide encoded by the cDNA contained in ATCC Deposit No. 75844; and (d) a polypeptide consisting of at least 50 contiguous amino acid residues of the polypeptide encoded by the cDNA contained in ATCC Deposit No. 75844;

wherein said isolated nucleic acid is linked to a heterologous polynucleotide encoding a heterologous polypeptide.

37. A recombinant vector comprising the isolated nucleic acid molecule of claim 31.

38. The recombinant vector of claim 37, wherein said nucleic acid molecule is operably associated with a heterologous regulatory sequence that controls gene expression.

39. The recombinant host cell comprising the isolated nucleic acid molecule of claim 31.

40. The recombinant host cell of claim 39, wherein said nucleic acid molecule is operably associated with a heterologous regulatory sequence that controls gene expression.

41. A method of producing a polypeptide, comprising:

(a) culturing a host cell under conditions suitable to produce a polypeptide encoded by the nucleic acid molecule of claim 31; and (b) recovering the polypeptide from the cell culture.

42. An isolated nucleic acid molecule comprising a polynucleotide sequence encoding a polypeptide selected from the group consisting of:

(a) a polypeptide comprising an amino acid sequence which is at least 95% identical to amino acids 1 to 212 of SEQ ID NO: 2; and (b) a polypeptide comprising an amino acid sequence which is at least 95% identical to the sequence of a polypeptide encoded by the cDNA contained in ATCC Deposit No. 75884.

43. The isolated nucleic acid molecule of claim 42, wherein said polynucleotide sequence encoding the polypeptide sequence is (a).

44. The isolated nucleic acid molecule of claim 42, wherein said polynucleotide sequence encoding the polypeptide sequence is (b).

45. The isolated nucleic acid molecule of claim 42, wherein said polynucleotide sequence comprises a heterologous polynucleotide sequence.

46. The isolated nucleic acid molecule of claim 45, wherein said heterologous polynucleotide sequence encodes a heterologous polypeptide sequence.

47. A recombinant vector comprising the isolated nucleic acid molecule of claim 42.

48. The recombinant vector of claim 47, wherein said nucleic acid molecule is operably associated with a heterologous regulatory sequence that controls gene expression.

49. A recombinant host cell comprising the isolated nucleic acid molecule of claim 42.

50. The recombinant host cell of claim 49, wherein said nucleic acid molecule is operably associated with a heterologous regulatory sequence that controls gene expression.

51. A method of producing a polypeptide, comprising:

(a) culturing a host cell under conditions suitable to produce a polypeptide encoded by the nucleic acid molecule of claim 42; and (b) recovering the polypeptide from the cell culture.

* * * * *

CERTIFICATE OF CORRECTION

PATENT NO. : 6,849,436 B2
DATED : February 1, 2005
INVENTOR(S) : Bednarik et al.

It is certified that error appears in the above-identified patent and that said Letters Patent is hereby corrected as shown below:

Title page,
Item [56], References Cited, OTHER PUBLICATIONS, please replace item 6 with the following, -- Genbank Entry Accession No. I06859 (1994) --

Column 34,
Lines 18-27, please replace Claim 42 with the following:
-- 42. An isolated nucleic acid molecule comprising a polynucleonde sequence encoding a polypeptide selected from the group consisting of:
(a) a polypeptide comprising an amino acid sequence which is at least 95% identical to amino acids 1 to 212 of SEQ ID NO.2; and
(b) a polypeptide comprising an amino acid sequence which is at least 95% identical to the sequence of a polypeptide encoded by the cDNA contained in ATCC Deposit No. 75844. --

Signed and Sealed this

Thirty-first Day of May, 2005

JON W. DUDAS
*Director of the United States Patent and Trademark Office*